(12) United States Patent
Lonky et al.

(10) Patent No.: US 8,915,894 B1
(45) Date of Patent: Dec. 23, 2014

(54) VACUUM CUP FOR DELIVERY OF AGENTS DURING VACUUM TREATMENT

(75) Inventors: Neal Marc Lonky, Yorba Linda, CA (US); Albert Steve Gurganian, Yorba Linda, CA (US)

(73) Assignee: Meditech Development Incorporated, Yorba Linda, CA (US)

( * ) Notice: Subject to any disclaimer, the term of this patent is extended or adjusted under 35 U.S.C. 154(b) by 0 days.

(21) Appl. No.: 13/450,464

(22) Filed: Apr. 18, 2012

Related U.S. Application Data

(60) Provisional application No. 61/476,861, filed on Apr. 19, 2011.

(51) Int. Cl.
- *A61M 1/00* (2006.01)
- *A61F 13/00* (2006.01)
- *A61M 35/00* (2006.01)

(52) U.S. Cl.
CPC ..................................... *A61M 35/00* (2013.01)
USPC ........... 604/290; 604/305; 604/313; 604/289; 604/304

(58) Field of Classification Search
CPC .......................... A61M 1/0058; A61M 1/0023
USPC .................. 604/290, 319, 305, 313, 289, 304
See application file for complete search history.

(56) References Cited

U.S. PATENT DOCUMENTS

| | | | |
|---|---|---|---|
| 1,294,284 A | 2/1911 | Longeman | |
| 1,460,927 A | 2/1922 | Thompson | |
| 2,082,782 A | 10/1933 | Allen | |
| 3,765,408 A | 10/1973 | Kawai | |
| 3,768,477 A | 10/1973 | Anders et al. | |
| 4,049,000 A | 9/1977 | Williams | |
| 4,278,348 A * | 7/1981 | Funk et al. | 355/73 |
| 4,314,560 A | 2/1982 | Helfgott et al. | |
| 4,957,484 A | 9/1990 | Murtfeldt | |
| 4,986,839 A | 1/1991 | Wertz et al. | |
| 5,019,086 A | 5/1991 | Neward | |
| 5,123,403 A | 6/1992 | Lavyne | |
| 5,124,364 A | 6/1992 | Wolff et al. | |
| 5,149,331 A | 9/1992 | Ferdman et al. | |

(Continued)

OTHER PUBLICATIONS

"Solvent Sealed Liquid Ring Vacuum Pumps". Wintek Corporation: Aug. 23, 2007. <http://www.wintek-corp.com/liquid-ring/solvent-sealed-liquid-ring.html>.*

(Continued)

*Primary Examiner* — Tatyana Zalukaeva
*Assistant Examiner* — Sara Sass
(74) *Attorney, Agent, or Firm* — Sci-Law Strategies, PC

(57) ABSTRACT

In various embodiments of the invention, the components can include a hemostatic vacuum cup which can utilize ancillary or self-contained vacuum generation, and a therapeutic agent which is supplied prior, simultaneously or subsequent to the application of a vacuum with the ultimate aim of slowing or arresting the flow of blood in a bodily tissue or organ. The invention relates to a hemostatic vacuum cup which can utilize ancillary or self-contained vacuum generation. The cup produces a hemostatic effect by the physical application of the device upon a traumatized tissue site and through the delivery of an agent, such as one that assists in hemostasis, antinociception, coagulation, sterilization, or other effective wound healing agents including antibiotics, antiseptics and antioxidants. The cup can be adapted to deliver the therapeutic agent, by methods integral to the vacuum cup. The therapeutic agent can be delivered in the form of a sponge, cellulose or other filter material.

20 Claims, 16 Drawing Sheets

(56) References Cited

U.S. PATENT DOCUMENTS

| | | | |
|---|---|---|---|
| 5,186,711 | A | 2/1993 | Epstein |
| 5,196,003 | A | 3/1993 | Bilweis |
| 5,224,947 | A | 7/1993 | Cooper et al. |
| 5,250,075 | A | 10/1993 | Badie |
| 5,259,836 | A | 11/1993 | Thurmond et al. |
| 5,281,229 | A | 1/1994 | Neward |
| 5,395,379 | A | 3/1995 | Deutchman et al. |
| 5,423,830 | A | 6/1995 | Chneebaum et al. |
| 5,472,426 | A | 12/1995 | Bonati et al. |
| 5,472,438 | A | 12/1995 | Schmit et al. |
| 5,507,752 | A | 4/1996 | Elliott |
| 5,636,643 | A | 6/1997 | Argenta |
| 5,643,183 | A | 7/1997 | Hill |
| 5,645,081 | A | 7/1997 | Argenta |
| 5,693,058 | A | 12/1997 | Cavanagh et al. |
| 5,727,569 | A | 3/1998 | Benetti et al. |
| 5,762,606 | A | 6/1998 | Minnich |
| 5,769,784 | A | 6/1998 | Barnett et al. |
| 5,799,661 | A | 9/1998 | Boyd et al. |
| 5,810,840 | A | 9/1998 | Lindsay |
| 5,836,311 | A | 11/1998 | Borst et al. |
| 5,865,730 | A | 2/1999 | Fox et al. |
| 5,865,827 | A | 2/1999 | Bullister |
| 5,885,271 | A | 3/1999 | Hamilton et al. |
| 5,891,017 | A | 4/1999 | Swindle et al. |
| 5,906,607 | A | 5/1999 | Taylor |
| 5,935,136 | A | 8/1999 | Hulse et al. |
| 6,074,399 | A | 6/2000 | Wallace et al. |
| 6,506,166 | B1 | 1/2003 | Hendler et al. |
| 6,755,780 | B2 | 6/2004 | Borst |
| 2010/0137775 | A1* | 6/2010 | Hu et al. ............... 602/54 |

OTHER PUBLICATIONS

Abboud, F., "Integration of Reflex Responses in the Control of Blood Pressure and Vascular Resistance", Am. J. Cardiol. 44:904-911 (1979).

Argenta, L.C. et al., "Vacuum-Assisted Closure: A New Method for Wound Control and Treatment: Clinical Experience", Ann. Plast. Surg. 38:563-577 (1997).

Bale, R.J. et al., "Minimally Invasive Head Holder to Improve the Performance of Frameless Stereotactic Surgery", Laryngoscope 107:373-377 (1997).

Chamberlain, G. et al., "ABC of Labour Care: Operative Delivery", British Med. J 318:1260-1264 (1999).

Chua Patel, C.T. et al., "Vacuum-Assisted Wound Closure", Am. J Nursing 100(12):45-48 (2000).

Jukema, G.N. et al., "Vacuum Sealing of Osteomyelitis and Infections of the Soft Tissue", Langenbecks Arch. Chir. Suppl. II 114:581-585 (Kongressbericht 1997).

Kim, E.D. et al., "Advances in the Treatment of Organic Erectile Dysfunction", Hosp. Pract. 32:101-120 (1997).

Klemm, B. et al., "Vacuum-Supported Endoscopic Access", End. Surg. 3:58-62 (1995).

Morykwas, M.J. et al., "Vacuum-Assisted Closure: A New Method for Wound Control and Treatment: Animal Studies and Basic Foundation", Ann. Plast. Surg. 38:553-562 (1997).

Muller, G., "Vacuum-Sealing Technique in Septic Surgery", Langenbecks Arch. Chir. Suppl. Kongressbd 114:537-541 (1997).

Mullner, "The Use of Negative Pressure to Promote the Healing of Tissue Defects: A Clinical Trial . . . ", Br. J. Plastic Surg. 50:194-199 (1997).

Peolosi, "Use of the Soft Silicone Obsteric Vacuum Cup to Facilitate Delivery and Maniupulatio of Large Pelvic . . . ", Am. J. Obsterics and Gynecology 148:337-339 (1984).

Sames, C.P. et al., "Sealing of Wounds with Vacuum Drainage", Br. Med. J. 2:1223 (197.

Smith, L.A. et al., "Vacuum Pack Technique of Temporary Abdominal Closure: A Four-Year Experience", Am. Surg. 63(12):1102-1108 (1977).

Soderdahl, D.W. et al., "The Use of an External Vacuum Device to Augment a Penile Prosthesis", Tech. Urol. 3(2):100-102 (1997).

Won, "Stereotactic Biopsy of Ductal Carcinoma In Situ of the Breast Using an 11-Gauge Vacuum-Assisted Device: Persisitent . . . ", Am J of Roentgenology 173:227-229 (1984).

* cited by examiner

VACUUM CUP FOR DELIVERY OF AGENTS DURING VACUUM TREATMENT

PRIORITY CLAIM

This application claims priority to U.S. Provisional Patent Application Ser. No. 61/476,861, entitled: "VACUUM CUP FOR DELIVERY OF AGENTS DURING VACUUM TREATMENT", inventors: Neal M. Lonky and A. Steve Gurganian, filed Apr. 19, 2011, which application is incorporated herein by reference in its entirety.

CROSS-REFERENCE TO RELATED APPLICATIONS

This application is related to the following applications:
(1) "SURGICAL VACUUM INSTRUMENT FOR RETRACTING, EXTRACTING, AND MANIPULATING TISSUE" by Neal M. Lonky, application Ser. No. 09/489,632, filed on Jan. 24, 2000, which issued on Nov. 4, 2003 as U.S. Pat. No. 6,641,575;
(2) "VACUUM INSTRUMENT FOR SLOWING OR ARRESTING THE FLOW OF BLOOD" by Neal M. Lonky, filed on Oct. 2, 2003, which issued on May 3, 20011 as U.S. Pat. No. 7,935,094; and
(3) "VACUUM INSTRUMENT FOR LAPAROTOMY PROCEDURES" by Neal M. Lonky, application Ser. No. 11/067,512, filed on Feb. 25, 2005, now abandoned; and
(4) "PORTABLE REGULATED VACUUM PUMP FOR MEDICAL PROCEDURES" by Neal M. Lonky et al., application Ser. No. 12/690,763, filed on Jan. 20, 2010, which applications (1)-(4) are explicitly incorporated herein by reference in their entireties.

FIELD OF THE INVENTION

This invention relates to the delivery of agents during the treatment of wounds or incisions wherein the agents are delivered via a vacuum cup attached to body parts and/or tissue to reduce blood loss from the wounds or incisions.

BACKGROUND OF THE INVENTION

Medicine is about saving lives and in this endeavor, the cutting edge focus is on the actions and resources available to emergency responders in life threatening situations and first aid medics is war zones. In Iraq, improvements in injury management, including better designed tourniquets and hemostat bandages, have significantly reduced fatalities. Rapid access to fresh whole blood and recombinant activated Factor VII also has reduced the likelihood that severely wounded combatants bled to death.

Bleeding or hemorrhaging is the loss of blood from the circulatory system. Bleeding can occur internally from blood vessels in organs inside the body. Alternatively, bleeding can occur externally through a disruption of the vasculature which could be concealed resulting in a hematoma, ore in the skin. Desanguination is a massive loss of blood from the body and results in acute blood loss anemia. The primary risk of desanguination is a reduction in the number of erythrocytes carrying hemoglobin and oxygen to the cells of the body. Typically, 100 mL of blood transports approximately 20 mL of oxygen. Various organs extract the amount of oxygen they require for normal functioning from the blood circulating through the organ. For example, the kidney, brain and heart extract approximately 2, 6.5 and 10.5 mL of oxygen per 100 mL of blood in circulation. When a person losses more than 20% of the total blood volume a lack of oxygen to the cells or hypoxia can occur. Hypoxia causes all blood vessels to dilate, speeding up the blood flow. The venus blood return to the heart increases, and as a result the heart works harder and faster trying to prevent cardiopulmonary congestion. Severe shock and lactic acidosis can result. Ultimately, if blood loss exceeds 40% to 50% of plasma volume, the resulting desanguination can lead to heart and circulatory failure and death. Initially, the body compensates for a rapid reduction in oxygen supply by extracting liquids and electrolytes from tissues and interstitial spaces to expand the volume of plasma and formation of new blood cells. This decreases the viscosity of blood which increases the risks of cardiac dilation, heart valve insufficiency and ventricular dysfunction. Severe bleeding can also reduce the amount of iron in the body to the extent that the bone marrow is unable to compensate for the loss of red blood cells. Bone marrow repletion of the blood supply takes significant time (weeks) which would not be relevant in an acute blood loss scenario likely to occur in a post traumatic setting.

SUMMARY OF THE INVENTION

In an embodiment of the present invention, a therapeutic agent is administered via a vacuum cup where the vacuum cup is applied to a body part, such that the therapeutic agent and the vacuum are used to reduce the hemorrhaging. The therapeutic agent applied through the vacuum cup can be advantageously used to apply a tamponade at a wound site, rupture, laceration, or other bleeding site. By applying a mild vacuum to the site, the target site is squeezed or compressed, transmitting a mild pressure which slows or arrests bleeding. In an embodiment of the present invention, by administering a therapeutic agent through the vacuum cup the therapeutic agent can allow a better vacuum to be applied to the wound site to allow the mild vacuum to function as a tamponade. In an alternative embodiment of the present invention, by administering a therapeutic agent through the vacuum cup the therapeutic agent can function together with the mild vacuum to tamponade the hemorrhaging. This procedure can be utilized both internally, and on external body surfaces as an advanced tamponade until the wound site can be otherwise repaired or treated.

In an embodiment of the present invention, the therapeutic agent and the vacuum can be applied with heating of the surrounding tissue to vasodilate. In an embodiment of the present invention, the therapeutic agent and the vacuum can be applied with cooling of the surrounding tissue to vasoconstrict. In an embodiment of the present invention, the therapeutic agent and the vacuum can be applied with removal of heating of the surrounding tissue to vasoconstrict. In an embodiment of the present invention, the therapeutic agent and the vacuum can be applied with removal of cooling of the surrounding tissue to vasodilate. In an embodiment of the present invention, by controlling the blood flow through applying heating the healing process can be improved. In an alternative embodiment of the present invention, by controlling the blood flow through applying cooling the healing process can be improved. In another embodiment of the present invention, by controlling the blood flow through applying both heating and cooling to the surrounding tissue the healing process can be improved. In an embodiment of the present invention, by alternatively applying heating and then cooling the healing process can be improved. In an embodiment of the present invention, chemical agents can be used to one or both heat and cool the surrounding tissue. In an embodiment of the present invention, physical processes can be used to one or both heat and cool the surrounding tissue.

In an embodiment of the present invention, both positive and negative pressure can be applied within the cup to the surrounding tissue to improve the healing process.

In an embodiment of the invention, a transferasome agent that promotes trans-epithelial absorption can be administered through the vacuum cup prior to or together with topical administration of an active agent. In an alternative embodiment of the invention, a transferasome agent that promotes trans-epithelial absorption can be administered through the vacuum cup prior to or together with subcutaneous administration of an active agent. In an embodiment of the invention, a transferasome agent that promotes trans-epithelial absorption can be administered through the vacuum cup prior to or together with other therapeutic modalities. In an embodiment of the invention, a transferasome agent can be used during therapy in cases where the would is closed. In an embodiment of the invention, a transferasome agent can be used during therapy in cases where the would is a subcutaneous hematoma. In an embodiment of the invention, the transferasome agent would be concentrated and delivered under the cup into the subcutaneous tissue where it would reach the vasculature and microvasculature and modulate the blood flow, affect coagulation, or deliver other therapeutic modalities. The purpose of the vacuum cup device is to compress and constrict the wound and deliver the drug or therapeutic agent in the region where tamponade is needed to augment or serve as a catalyst to the therapy.

BRIEF DESCRIPTION OF THE DRAWINGS

This invention is described with respect to specific embodiments thereof. Additional features can be appreciated from the Figures in which.

DETAILED DESCRIPTION OF THE INVENTION

Figure 1:
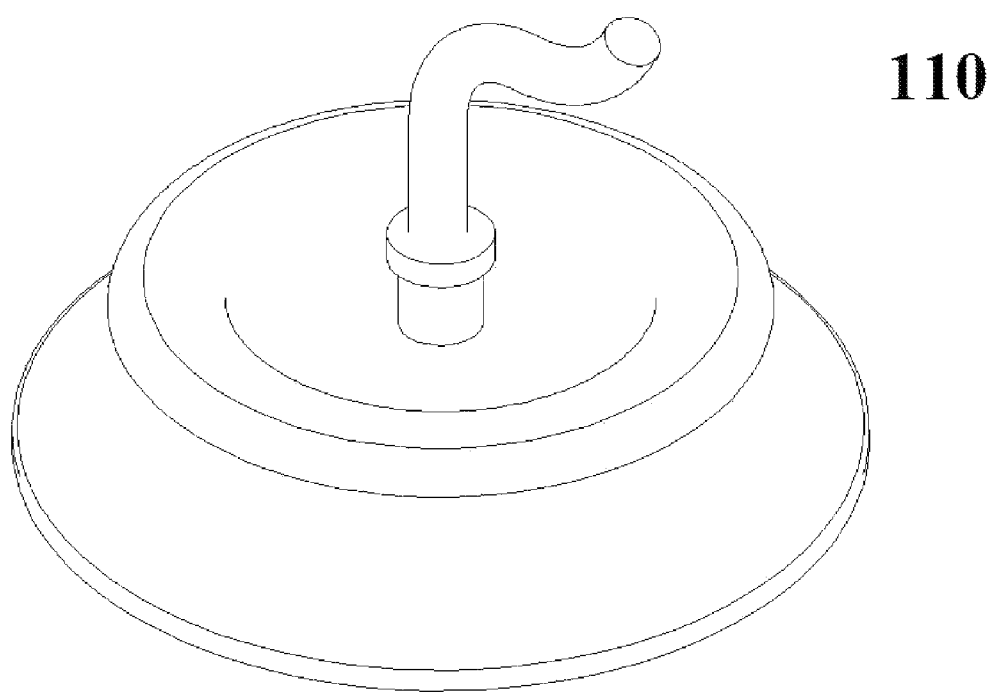
FIG. 1 is a schematic drawing of a vacuum cup in accordance with an embodiment of the invention.

In the following description, various aspects of the present invention will be described. However, it will be apparent to those skilled in the art that the present invention can be practiced with only some or all aspects of the present invention. For purposes of explanation, specific numbers, materials, and configurations are set forth in order to provide a thorough understanding of the present invention. However, it will be apparent to one skilled in the art that the present invention can be practiced without the specific details. In other instances, well-known features are omitted or simplified in order not to obscure the present invention.

Parts of the description will be presented in data processing terms, such as data, selection, retrieval, generation, and so forth, consistent with the manner commonly employed by those skilled in the art to convey the substance of their work to others skilled in the art. As is well understood by those skilled in the art, these quantities (data, selection, retrieval, generation) take the form of electrical, magnetic, or optical signals capable of being stored, transferred, combined, and otherwise manipulated through electrical, optical, and/or biological components of a processor and its subsystems.

Various operations will be described as multiple discrete steps in turn, in a manner that is most helpful in understanding the present invention; however, the order of description should not be construed as to imply that these operations are necessarily order dependent.

Various embodiments will be illustrated in terms of exemplary classes and/or objects in an object-oriented programming paradigm. It will be apparent to one skilled in the art that the present invention can be practiced using any number of different classes/objects, not merely those included here for illustrative purposes. Furthermore, it will also be apparent that the present invention is not limited to any particular software programming language or programming paradigm.

Systems and methods in accordance with embodiments of the present invention can provide for improved presentation and interaction with digital content and representations of digital content. Representation as used herein includes, but is not limited to, any visual and/or audible presentation of digital content. By way of a non-limiting example, digital images, web pages, digital documents, digital audio, and other suitable content can have corresponding representations of their underlying content. Moreover, interfaces such as graphical user interfaces can have corresponding representations of their underlying content.

The invention is illustrated by way of example and not by way of limitation in the figures of the accompanying drawings in which like references indicate similar elements. It should be noted that references to 'an' or 'one' embodiment in this disclosure are not necessarily to the same embodiment, and such references mean at least one.

A vacuum of atmospheric pressure is 1 atmosphere=760 torr. Generally, "approximately" in this pressure range encompasses a range of pressures from below $7.6\times10^3$ torr to $7.6\times10^1$ torr. A pressure of below $10^{-3}$ torr would constitute a high vacuum. A pressure of below $10^{-2}$ torr would constitute a medium vacuum. A pressure between atmospheric pressure and a medium vacuum constitutes a low vacuum. In an embodiment of the invention a vacuum is sensed at a suction device 110. In an alternative embodiment of the invention a vacuum is sensed at a wound 566. In an alternative embodiment of the invention a vacuum is sensed at a site of trauma 566. In another embodiment of the invention a vacuum is sensed at a tissue. In an embodiment of the invention the vacuum sensed at the tissue compensates for out-gassing and leaks when the suction device is applied to the tissue. Generally, "approximately" in a low vacuum pressure range encompasses a range of pressures from between $5\times10^{-1}$ torr to $5\times10^{-2}$ torr. Generally, "approximately" in a medium vacuum pressure range encompasses a range of pressures from between $5\times10^{-2}$ torr to $5\times10^{-3}$ torr. In an embodiment of the invention, a marginal increase in vacuum is an increase of vacuum from $10^{-1}$ torr to $5\times10^{-2}$ torr. In an alternative embodiment of the invention, a marginal increase in vacuum is an increase of vacuum from $5\times10^{-2}$ torr to $10^{-2}$ torr. The vacuum device can operate to lower the pressure from atmospheric pressure to generate a high vacuum. In an embodiment of the invention, a low vacuum can be applied in, for example, obstetric suction devices. In an embodiment of the invention, a medium vacuum can be applied in, for example, orthopedic suction devices. In an embodiment of the invention, immediate release of a low vacuum reduces the vacuum to approximately atmospheric pressure in between a lower limit of approximately 0.1 second and an upper limit of approximately 0.5 second. In an embodiment of the invention, immediate release of a medium vacuum reduces the vacuum to approximately atmospheric pressure in between a lower limit of approximately 0.3 second and an upper limit of approximately 1.0 second. In an embodiment of the invention, a force of approximately $10^2$ Newton can be applied to tissue with the vacuum cup. In an alternative embodiment of the invention, a force of approximately $10^3$ Newton can be applied to tissue with the vacuum cup. The tissues can include epithelial layers, organs, osseous tissue, bony tissue and connective tissue exposed by an open incision during a laparotomy, thoracotomy, craniotomy, retroperitoneal surgery and orthopedic vacuum fraction or manipulation of bony surfaces. The parameters used during application of a vacuum cup to a bleeding wound site include the nature of tissue, evenness of the surface, vacuum leak due to uneven surface, size of specific vacuum cup, type of specific vacuum cup, force applied to vacuum cup, time duration of vacuum applied and vacuum applied.

As used herein, the term "vacuum cup" refers to a device adapted to apply one or both positive and negative pressure to tissue in contact with or in proximity with the vacuum cup.

As used herein, the term "temperature pump" refers to a device adapted to heat and/or cool tissue in contact with or in proximity with the vacuum cup.

As used herein, the term 'water of hydration releasing material' refers to a chemical which either releases into or absorbs energy from the atmosphere concomitant with becoming solvated.

As used herein, the term 'phase change material' refers to a chemical which either releases into or absorbs energy from the atmosphere concomitant with a change is phase.

As used herein, the term 'hydration material' refers to a chemical which either releases or absorbs energy from the atmosphere concomitant with becoming hydrated. The enthalpy of hydration of an ion is the amount of energy released when a mole of the ion dissolves in a large amount of water forming an infinite dilute solution in the process. The molar enthalpy of solvation is the energy released when one mole of a solid is dissolved in a solvent. As used herein, the term 'reactive material' refers to a chemical which either releases or absorbs energy from the atmosphere concommitant with reacting with another chemical.

As used herein, the term 'efflorescent material' refers to a chemical which releases water to the atmosphere. As used herein, the term 'hygroscopic material' refers to a chemical which absorbs water from the atmosphere.

Polyvinyl alcohol (PVA) and polyvinylpyrrolidone (PVP) are water soluble synthetic polymer which are stable up to 100 degrees Celsius and are fully hydrolysable. PVA and PVP can be used to release an active agent upon the requisite presence of water or moisture. A complex between PVP and polymaleic diacid-alkyl vinyl ether (PMDV) in 1:1 ratio can be used to generate a controlled release of an active agent.

As used herein, the term 'transferasome agent' includes ethanol, methanol, n-propanol, isopropanol, other alcohols, dimethylsulfoxide, methylsulfonylmethane, and recombinant hyaluronidase for enhancing subcutaneous delivery of agents into tissue. Hyaluronidase degrades hyaluronan as structural component of tissue allowing increased penetration of other active agents. Hyaluron is reconstituted continually and therefore the increased penetration resulting from hyaluronidase treatment is a temporary effect.

The vacuum cup can be utilized in procedures which are intra- or extra-cavity, that is, procedures which involve body surfaces, orifices, or internal organs, and in both laparotomy and laparoscopic procedures.

In an embodiment of the invention, the device method or system can be used for the treatment of humans. In an embodiment of the invention, the device method or system can be used for the treatment of animals. In an embodiment of the invention, the device method or system can be used in veterinary applications. In an embodiment of the invention, the device method or system can be used in medical applications.

Figure 12:
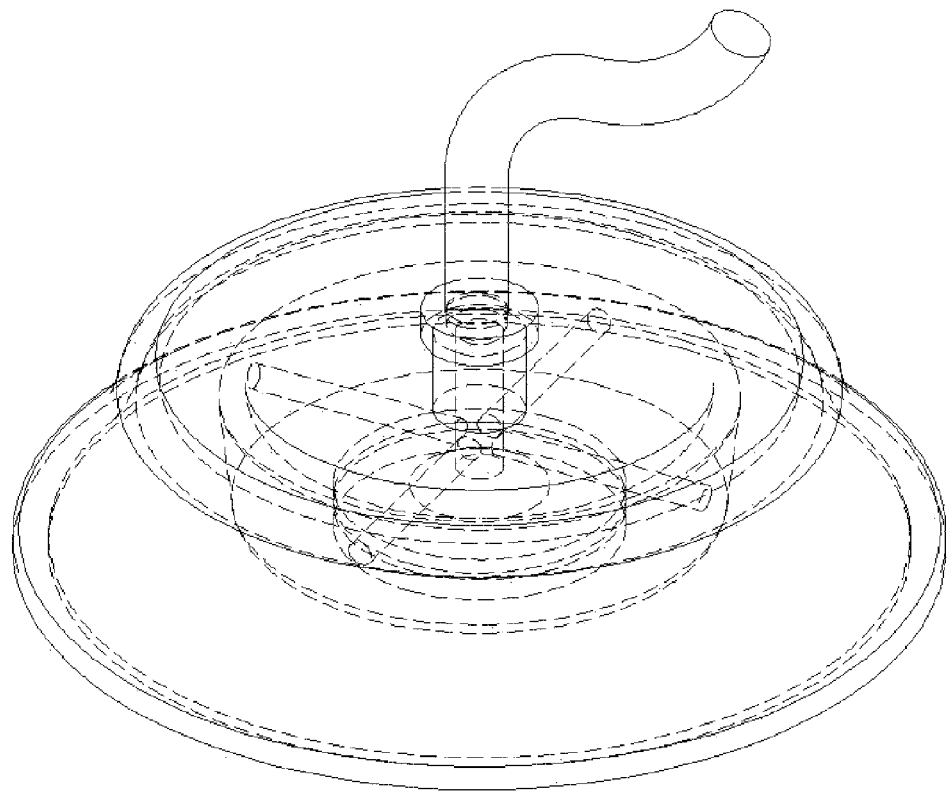
FIG. 12 is a schematic drawing of the vacuum cup insitu, in accordance with an embodiment of the invention.

The treatment of open wounds too large to spontaneously close have long been a troublesome area of medical practice. The initial stage of healing is characterized by the formation of granulation tissue which can take several hours. When an open wound is present or formed during surgery, it is not feasible to wait for normal wound healing. In order to help address this situation, application of vacuum has been proposed as a sealing device for the abnormal tissue. If a tissue displays a site which is bleeding, a suction cup can be applied at that site to tamponade active bleeding until surgery can be used to repair or remove the structure in question. As shown in FIG. 12 the vacuum cup can be at least partially transparent. In an alternative embodiment of the invention, the vacuum cup contains material with a window to view the wound. In an embodiment of the invention, if the trauma site or the peripheral margin of the wound is observed to have a bluish hue, or dusky grey appearance to the tissue, then it can be concluded that the appearance shows signs of "ischemia" and appropriate action can be taken including administering agents that will address the ischemia or lack of oxygenation to the cells.

When a vacuum is applied to a suction cup on a structure having a blood flow, blood can typically pool inside the site, which can lead to the formation of a hematoma. When an obstetrical vacuum extractor is applied to a fetal scalp during vacuum extraction-assisted deliveries of newborns, for example, occasionally a small bruise or hematoma occurs on the scalp. Additionally, some soft tissue edema and swelling can occur on the area of the scalp where the vacuum was applied.

There is a significant need for vacuum-assisted devices for use by emergency responders, first aid medics, obstetricians and surgeons carrying out internal medical procedures. Some examples of vacuum-assisted devices include vacuum cups, grasping cups, tamponade apparatuses, and suction cups that attach to body tissues. The vacuum-assisted devices can readily be applied in trauma situations where facilities are unavailable for full treatment of the wound. In an era when blood loss can necessitate transfusion, and transfusion can introduce pathogens such as the AIDS and hepatitis virus to the recipient, any strategy which can efficiently curtail or arrest blood loss as a temporizing method prior to or during surgery can add to the resources available to emergency responders in life threatening situations and first aid medics in war zones.

Before describing the invention in detail, it is helpful to describe an example environment in which the invention can be implemented. The present invention is particularly useful for emergency responders or first aid medics where the procedure requires that a vacuum cup be attached to the body of a patient or a victim with a bleeding wound. When a first responder or first aid medic attempts to apply a vacuum to a bleeding wound to reduce the blood loss a number of difficulties are encountered. Firstly, the surface of the wound to which the vacuum cup is to be applied is not sterile. Attempts to sterilize the wound can be confounded by the blood released by the wound. In addition, the blood can clog or otherwise disrupt the ability of a prior art cup to form a vacuum seal. In various embodiments of the invention, a vacuum cup with a dispensing seal can allow the emergency responder or first aid medic to dispense a therapeutic agent to increase the vacuum seal at the site of the wound in order to improve the vacuum applied to the wound. In various embodiments of the invention, a vacuum cup with a dispensing sponge can allow the emergency responder or first aid medic to dispense a therapeutic agent at the site of the wound while the vacuum is applied to the wound. In various embodiments of the invention, a vacuum cup able to dispense a therapeutic agent can also be used in existing surgical and obstetrical delivery procedures that require suction devices including vacuum cups, grasping cups, a tamponade apparatus, or other fixtures that attach to body tissue. Each of these devices requires a vacuum to be applied to attach the suction device to tissue. The vacuum can be supplied by a pump.

In an embodiment of the invention the first responder might notice a closed wound with an expanding hematoma noticeable in the subcutaneous space. Several chemical moieties known as transferasomes can deliver drugs or agents via patches, creams, or biofilms that would penetrate under the site of application. The wound could be treated with this agent while simultaneously being covered and then constricted or compressed using the vacuum cup methodology.

Figure 2:
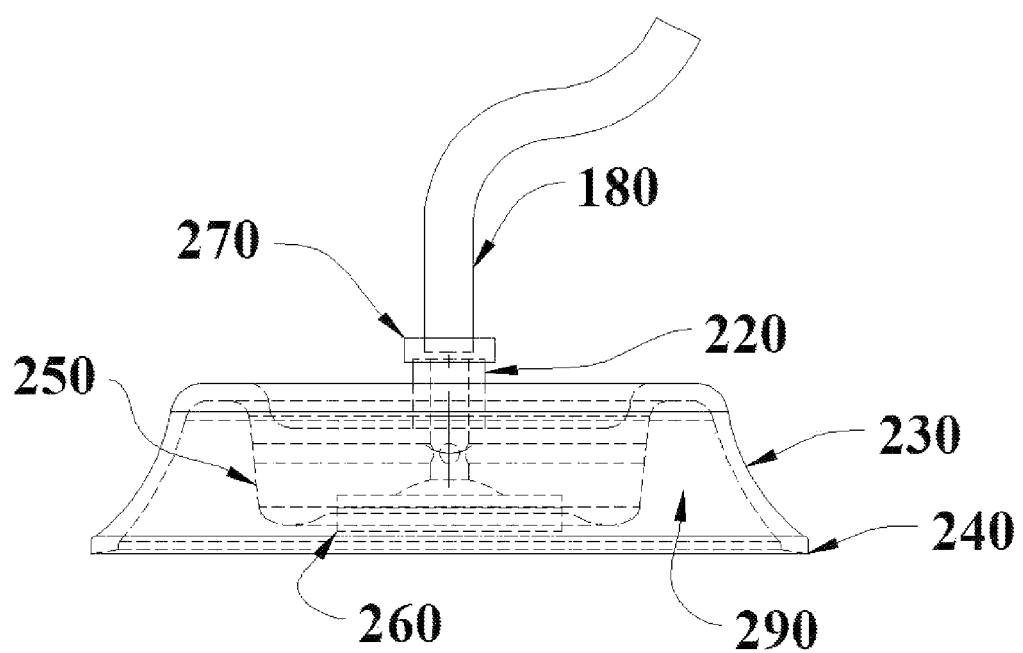
FIG. 2 is a schematic profile of the vacuum cup in accordance with an embodiment of the invention.

As shown in FIGS. 1 and 2, the vacuum cup 110 includes a top 220 and base 240 with a connecting side wall 230 that defines a hollow interior cavity 290. As shown in FIGS. 3 through 6, the base 240 is comprised of one or more annular rings which define the primary tissue 555 contact area. In an embodiment of the invention, within the hollow cavity 290, one or more projected surfaces including 250 provide one or more secondary tissue contact surfaces including 312. In an embodiment of the invention, cavities within the vacuum cup including the projected surfaces 312, the cup wall 230, or the top 220 can contain agents that can be released to the trauma site upon utilization of the vacuum cup 110. In an embodiment of the invention, the design can apply the vacuum force supplied to, or by the cup, against the tissue site providing axial compression and radial constriction. The compressive action delivers the contained agent directly to the trauma site.

In an embodiment of the invention, the primary purpose of applying the vacuum cup is to arrest the flow of blood to enable one or more of the first responders to undertake emergency stabilization procedures. In an alternative embodiment of the invention, the primary purpose of applying the cup is to arrest the flow of blood while triage is undertaken to determine the priority of treatment for a number of patients. A secondary purpose of applying the vacuum cup is to replace traditional bandages or compresses used with an actively bleeding wound. Often in emergency situations medical personnel are a scarce resource and a conscious patient can be asked to hold a compression bandage on a bleeding wound. If the patient looses consciousness, then the necessary compression is not supplied and significant blood loss can result. In this embodiment of the invention, the vacuum cup acts as a method to reliably reduce bleeding while not otherwise requiring personnel to attend or monitor the stabilization of the wound. A tertiary purpose of applying the vacuum cup is to provide an integral drug delivery haemostatic treatment that simplifies the process of dressing, treating and/or resolving a trauma site. A quaternary purpose of applying the vacuum cup is to provide a disposable haemostatic vacuum cup that can be inexpensively produced and stored for a long term. In this embodiment of the invention, emergency responders can routinely carry a vacuum cup that is hermetically sealed and can be removed from the hermetically sealed package and used when required. A quinary purpose of applying the vacuum cup is to provide a haemostatic vacuum cup that is easy to use and can utilize existing vacuum pump devices. The vacuum cup can be applied to provide one or more of the primary through quinary purposes.

Figure 3:
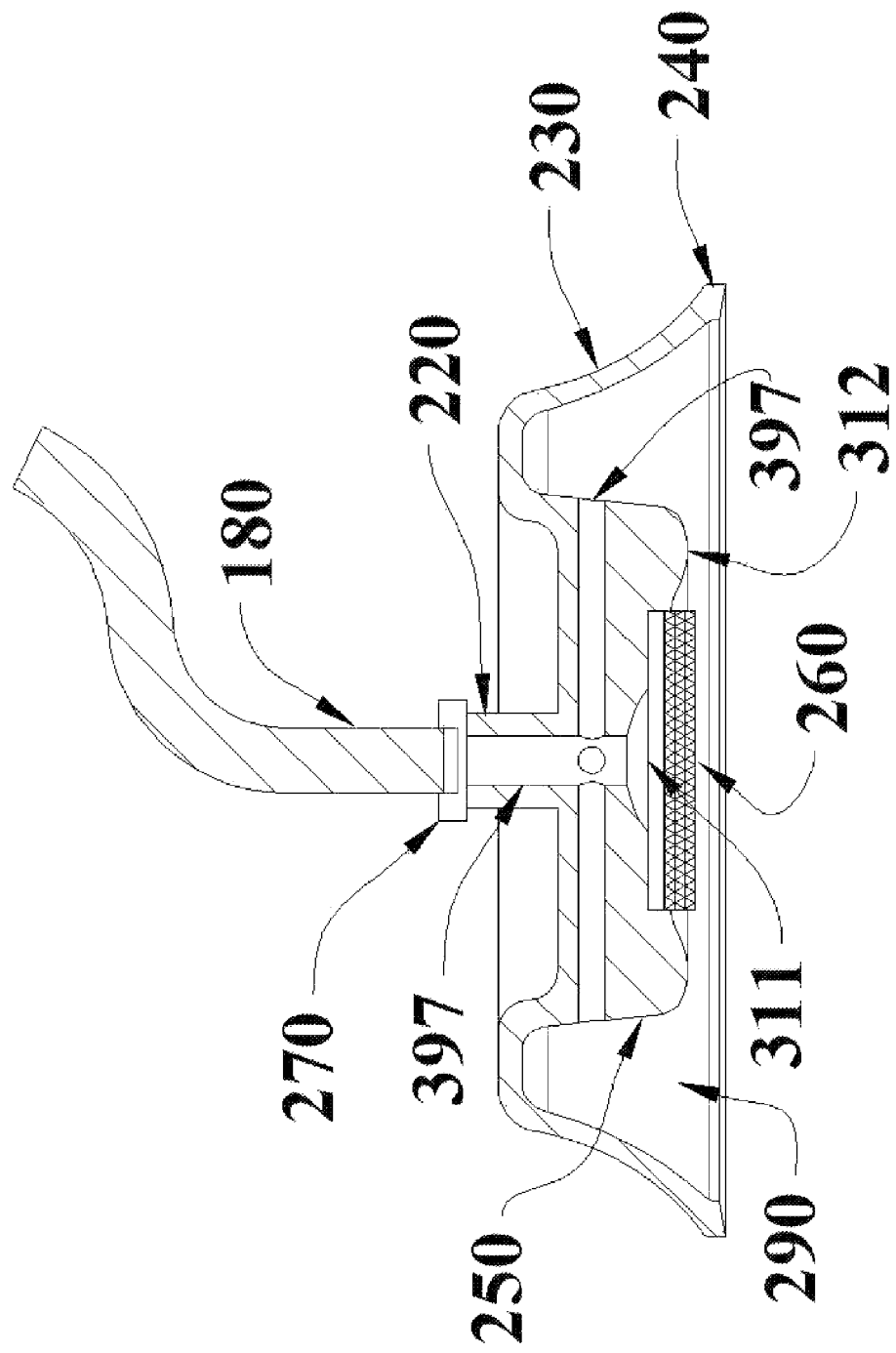
FIG. 3 is a schematic cross section of a vacuum cup in accordance with an embodiment of the invention.
Figure 4:
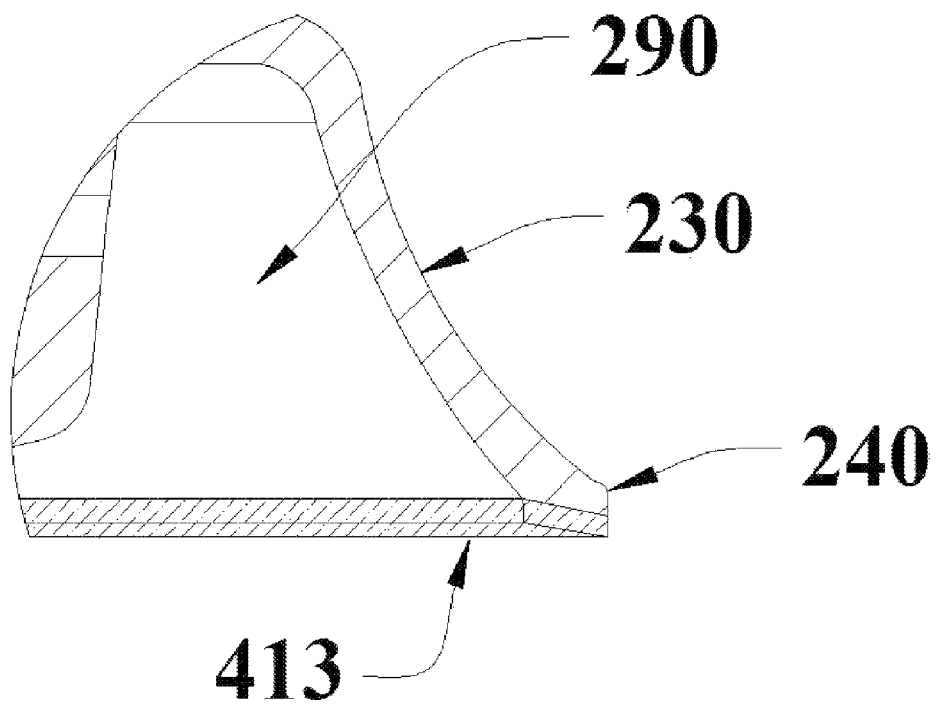
FIG. 4 is a schematic drawing of the base, walls and a cavity of a vacuum cup in accordance with an embodiment of the invention.
Figure 5:
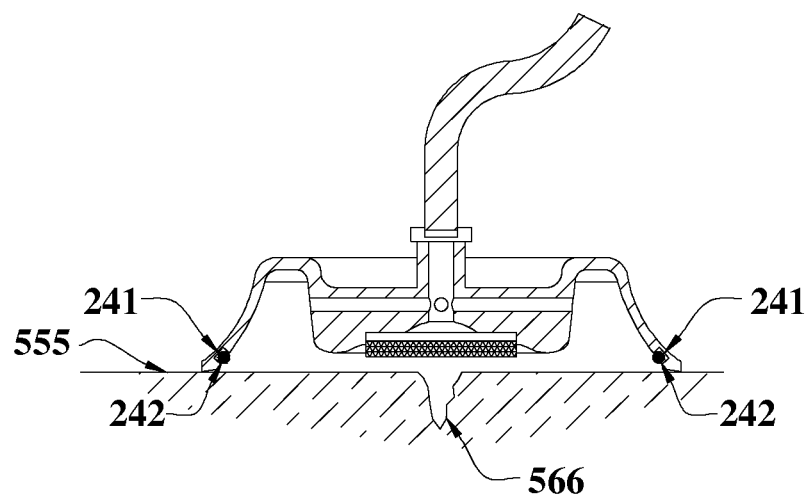
FIG. 5 is a schematic drawing of a vacuum cup applied to a tissue surface in which a trauma has been sustained, prior to application of a vacuum in accordance with an embodiment of the invention.
Figure 6:
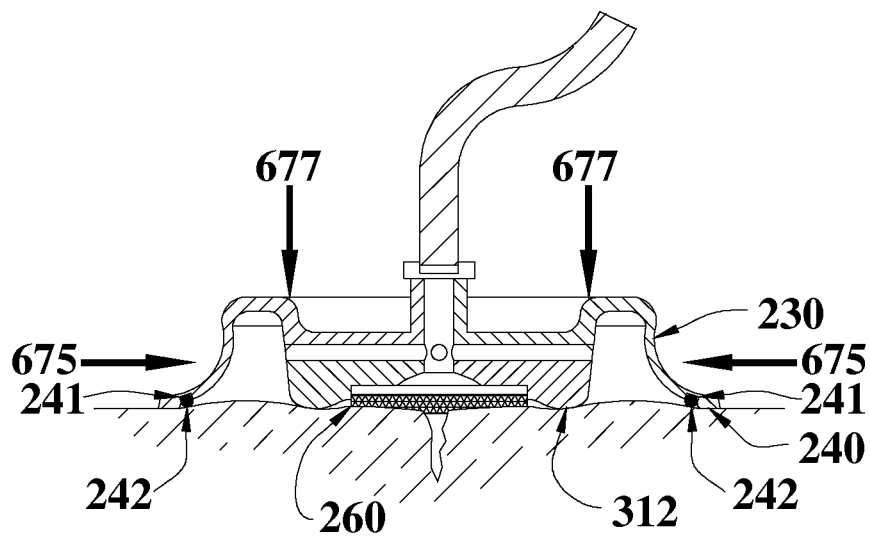
FIG. 6 is a schematic drawing of a vacuum cup with vacuum applied to a tissue surface in which a trauma has been sustained in accordance with an embodiment of the invention.

In an embodiment of the invention, the hollow cavity 290 within the cup wall provides at least one projection 250 perpendicular to the top 220 of the cup 110. The projections can be arranged as concentric rings or cylinders with annular distal bases. The base 240 and projection surface 312 can be comprised of flat, angular, concave, convex or ridged annular edges to provide an effective seal when in contact with the affected tissue. The cup 110 and the projection 250 are provided in varying sizes and shapes in a kit to meet the needs of differing trauma sites 566 and tissues types 555. In an alternative embodiment of the invention, a one size fits all vacuum cup 110 can be utilized. As shown in FIGS. 4-6, upon application of vacuum to the cup 110, the side walls 230 deform in a controlled collapse that applies inward radial pull 675 on the tissue 555 in contact with the cup's 110 primary annular base 240. The contact surface of the base 240 is initially fixed at an acute angle with respect to the perpendicular of the affected tissue surface 555. Upon application of vacuum pressure to the cup 110, the deformation of the side wall 230 rotates the annular base 240 bringing to bear the full surface area of the base 240 against the affected tissue to create an effective seal. The collapse of the cup wall 230 draws the tissue against the interior projection 250 which effectively applies axial pressure 677 to the trauma site. In an embodiment of the invention, as shown in FIG. 3, the distal surface 312 of the projection 250 includes a cavity 311 that can contain the agent to be delivered. In an embodiment of the invention, the delivered agent can be stored in the cup projection cavity in powder, liquid, gel or other forms. In an embodiment of the invention, the delivered agent can be contained in an impregnated open cell foam pad, gel, biofilm, cream, impregnated polymer, cloth, or other absorbent medium 260 within the cup including cavities 290 and/or 311. In an alternative embodiment of the invention, the delivered agent can be supplied to tissue that contacts the projection surface 312 when vacuum is applied to the cup 110. In another embodiment of the invention, the delivered agent can be generally supplied to all tissue surfaces enclosed within the cup.

The vacuum is provided to one or more chambers within the cup by channels 397 to insure vacuum supply to wall 230 and projection cavities 290 and/or 311. The vacuum channels 397 can be of diminished dimensions within the cup interior to insure proper primary wall 230 collapse and secondary projection 250 pressure. That is, in an embodiment of the invention, wall cavity vacuum channels can provide a greater vacuum for evacuation, e.g., a greater vacuum in the volume of one or more cavities. In an embodiment of the invention, the supply of vacuum pressure is to the top 220 center of the cup to insure a unified and proportional evacuation of the chambers. The vacuum can also be supplied at different locations on the body of the cup 110, with channels 397 provided as required to the interior cavities 290 and/or 311. In an embodiment of the invention, the vacuum pressure can be applied to the cup 110 by an attachment port 270 integral to the body of the cup 110. In an embodiment of the invention, the location of the port 270 is the top center of the cup 110. In an embodiment of the invention, the vacuum can also be supplied through a flexible tube 180 that is integral to the cup. The cup vacuum port 270 can contain a check valve (not shown) to insure the applied vacuum is maintained when applied from an external or integral source. The check valve can be constructed as an integral part of the cup 110 or as a separate component bonded to or within the cup 110 body.

In various embodiments of the invention, the cup 110 body components including the top 220, side wall 230, base 240 and projections 250 are made from a flexible elastomeric material such as silicone, natural rubber, nitrile, neoprene or other thermoplastics. In various embodiments of the invention, the cup 110 material can have durometer hardness values between a lower limit of approximately 10 Shore-00 and an upper limit of approximately 50 Shore-D. In an embodiment of the invention, each cup 110 body component has the same Shore values. In an alternative embodiment of the invention, some cup 110 body components have different Shore values. In another embodiment of the invention, each cup 110 body component has different Shore values.

In an embodiment of the invention, the primary contact surface 555 of the cup base 240 can be covered with a sealing material 413, as shown in FIG. 4, comprised of a soft elastomeric material, adhesive, or other flexible compound to insure an effective seal. In an embodiment of the invention, the covering material can be adhered to the base 240 by means well known to a person skilled in the arts, including sealants, adhesives, cements and natural glues, or can be an integral part of the base 240.

In various embodiments of the invention, the vacuum cup 110 can allow grasping of tissue 555 or the tissue surface 555 of organs prior to or during various types of surgery. Any organ or structure that has a smooth surface to which a vacuum device can attach and manipulate can be a candidate for use with the vacuum cup 110. Further, an organ or structure that has a rough surface can be addressed by adhering the covering material to the base 240. For example, when a suction device is applied to a fetal scalp on which lanugo, vellus or terminal hair is present; the hair can disturb the seal between the suction device and the scalp and thereby result in a vacuum leak. Application of a covering material can allow a constant vacuum enabling traction, extraction, and manipulation of the fetal head.

Figure 7:
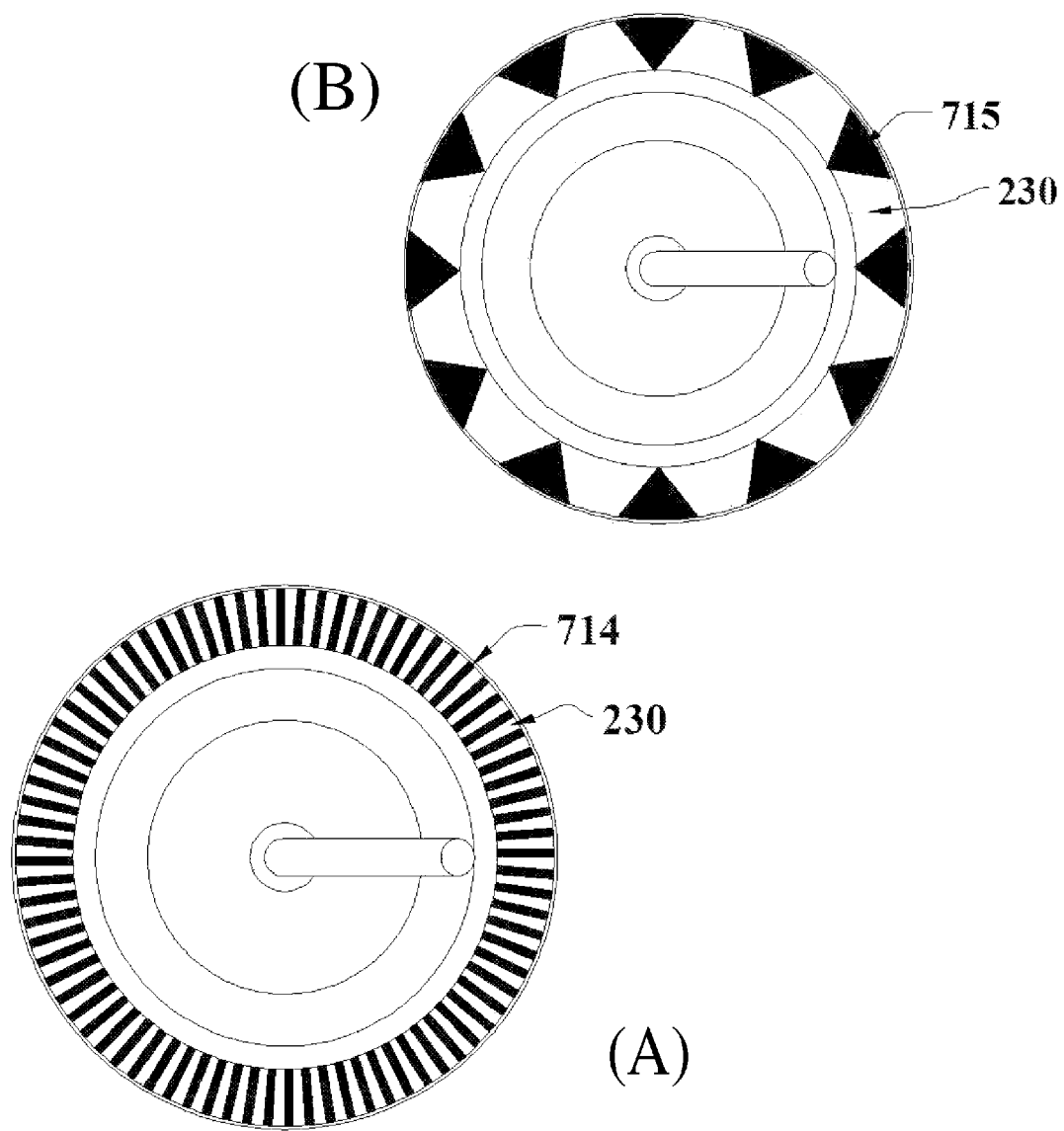
FIG. 7(A) is an overhead view of a vacuum cup in accordance with an embodiment of the invention.
FIG. 7(B) is an overhead view of a vacuum cup in accordance with an embodiment of the invention.

In an embodiment of the invention, as shown in the overhead schematic of a vacuum cup in FIG. 7(A), the cup wall 230 can be constructed with concentric ridges 714 perpendicular to the base. The ridges 714 can possess the same durometer characteristics as the wall 230, or have differing Shore values. In an embodiment of the invention, the cross section geometry of the ridges 714 can be circular, rectangular, angular or a combination of geometries. In an embodiment of the invention, the ridges 714 can be constructed with equal or greater thickness compared to the non-ridged areas of the cup wall 230.

In an embodiment of the invention, as shown in the overhead schematic of a vacuum cup in FIG. 7(B), the cup wall 230 can be constructed with concentric areas or panes 715 with respect to the base. These panes can possess the same durometer characteristics as the wall 230, or have differing Shore values. The pane 715 face geometry can be circular, rectangular, angular or a combination of geometries. The panes 715 can be constructed with equal or greater thickness compared to the non-paned areas of the cup wall 230.

In an embodiment of the invention, the cup wall 230 ridges 714 and panes 715 can be used to provide a controlled deformation of the cup 110 when placed under vacuum pressure. In an embodiment of the invention, the deformation can create the desired axial pressure 677 and radial pull 675 against the affected trauma site 566 tissue 555.

Figure 8:
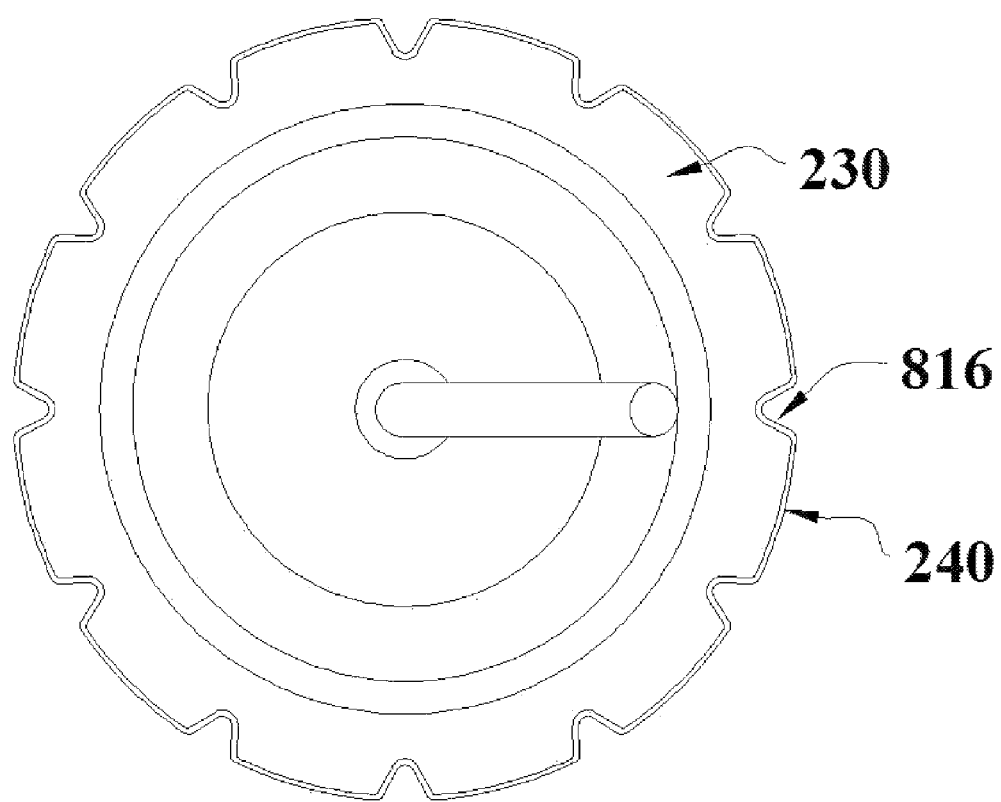
FIG. 8 is an overhead view of a vacuum cup in accordance with an embodiment of the invention.
Figure 9:
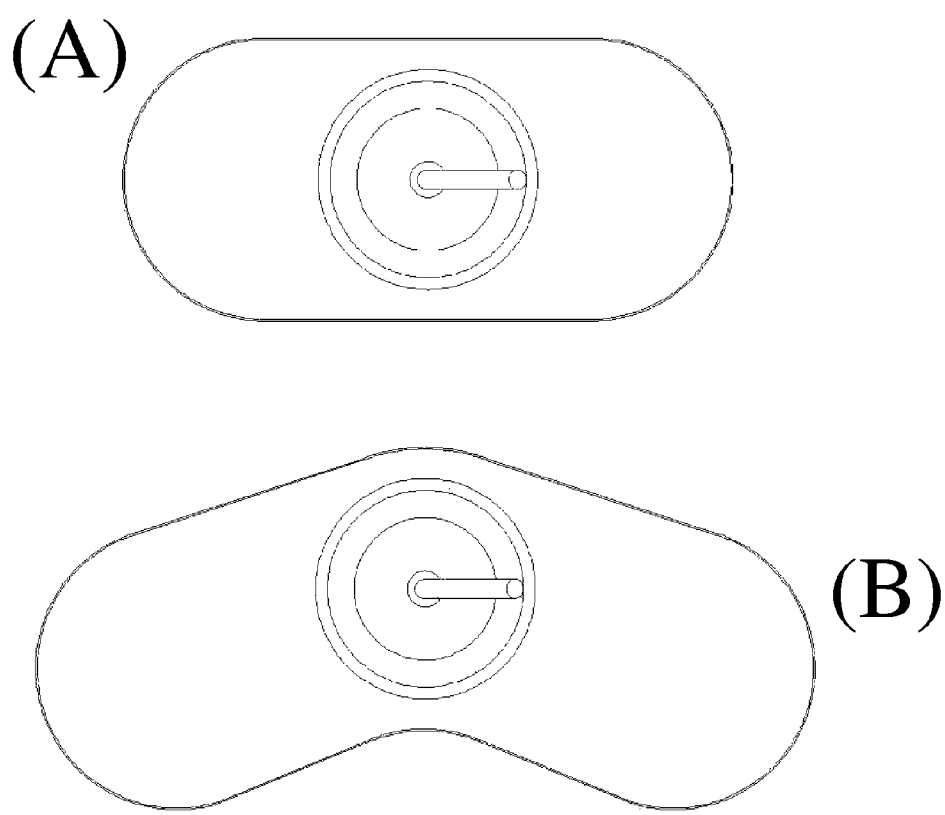
FIG. 9(A) is an overhead view of a vacuum cup in accordance with an embodiment of the invention.
FIG. 9(B) is an overhead view of a vacuum cup in accordance with an embodiment of the invention.

In an embodiment of the invention, as shown in the overhead schematic of a vacuum cup 110 in FIG. 8, the base 240 can be constructed with concentric indentations or notches 816 forming an annular pattern with respect to the cup wall 230. The notches can be of any geometric shape creating a contiguous contour of the base 240 surface contact area. As shown in the overhead schematic of a vacuum cup 110 in FIG. 9, the cup 110 overall shape can be of any geometry or size (not shown) including all aspects of the cup body components.

Figure 10:
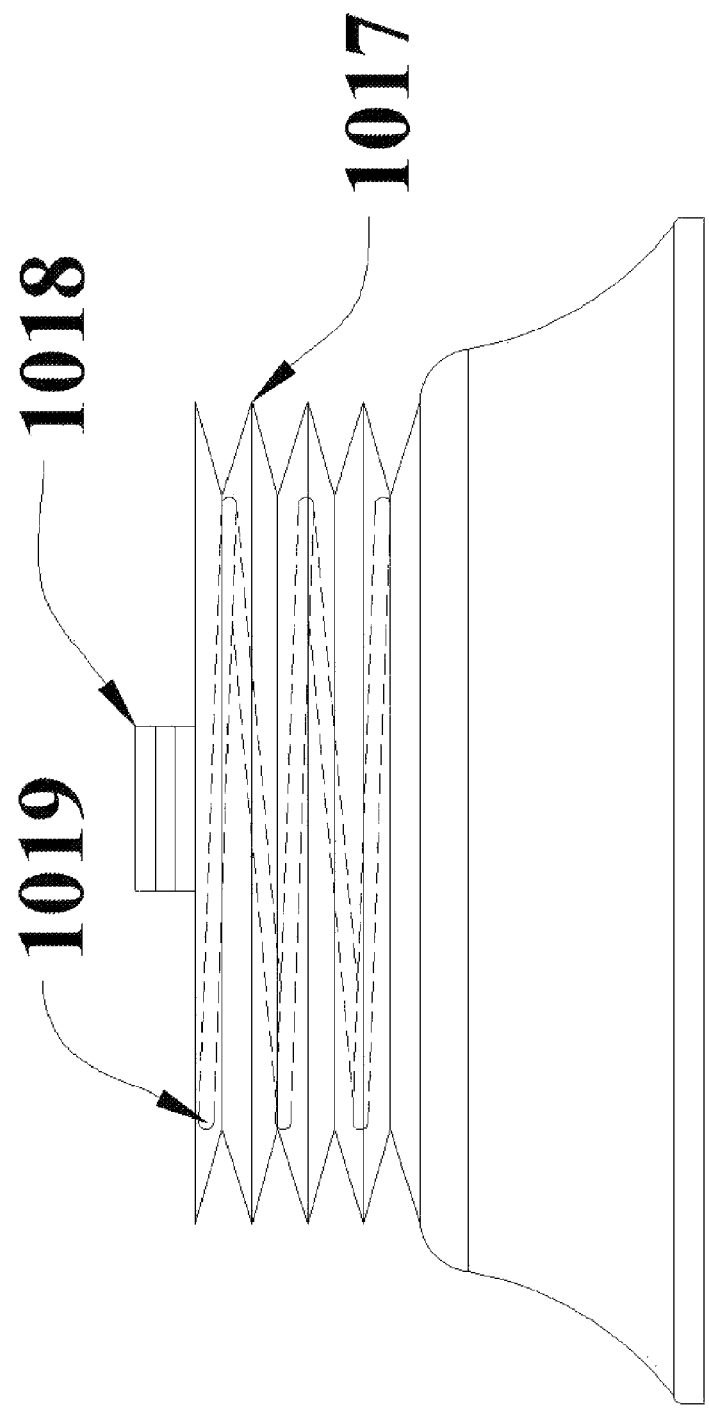
FIG. 10 is a schematic profile of a vacuum cup and vacuum device in accordance with an embodiment of the invention.

As shown in the side view of a vacuum cup 110 in FIG. 10, the cup 110 can include a mechanical hand actuated integral vacuum generation device. In an embodiment of the present invention, an integral bellows 1017 forms a part of the cup 110. In an embodiment of the invention, the bellows 1017 can be constructed of a flexible material such as silicone, natural rubber, nitrile or other thermoplastics allowing repeated compression and expansion while maintaining air-tight operation. The bellows 1017 includes an internal spring 1019 return component and an air exhaust valve 1018. Upon user hand depression of the bellows 1017, both the body of the bellows 1017 and the spring 1019 are compressed. The exhaust valve 1018 provides for the one-way escape of air within the bellows 1017 cavity when compressed. Release of the bellows 1017 by the user allows the spring 1019 to exert upward force against the bellows 1017 internal cavity, creating an effective vacuum pressure. The bellows 1017 internal cavity can be internally connected to the vacuum port 270 providing the direct supply of the generated vacuum pressure to the cup vacuum channels 397.

In an embodiment of the invention, the hand actuation of the bellows 1017 can provide an effective downward force upon the cup 110 essentially transforming the cup 110 from a vacuum cup to a suction cup. This hand action will force the evacuation of the cup cavities 290 and/or 311 initiating the haemostatic and active agent delivery actions. Release of the bellows 1017 allows the resultant vacuum pressure created to maintain internal cavity 290 and/or 311 operational vacuum pressures. In an embodiment of the invention, external vacuum generating devices can be connected to the exhaust valve 1018 to provide continued unattended vacuum pressure to the cup 110 following the initial user hand activation of the bellows 1017.

Figure 11:
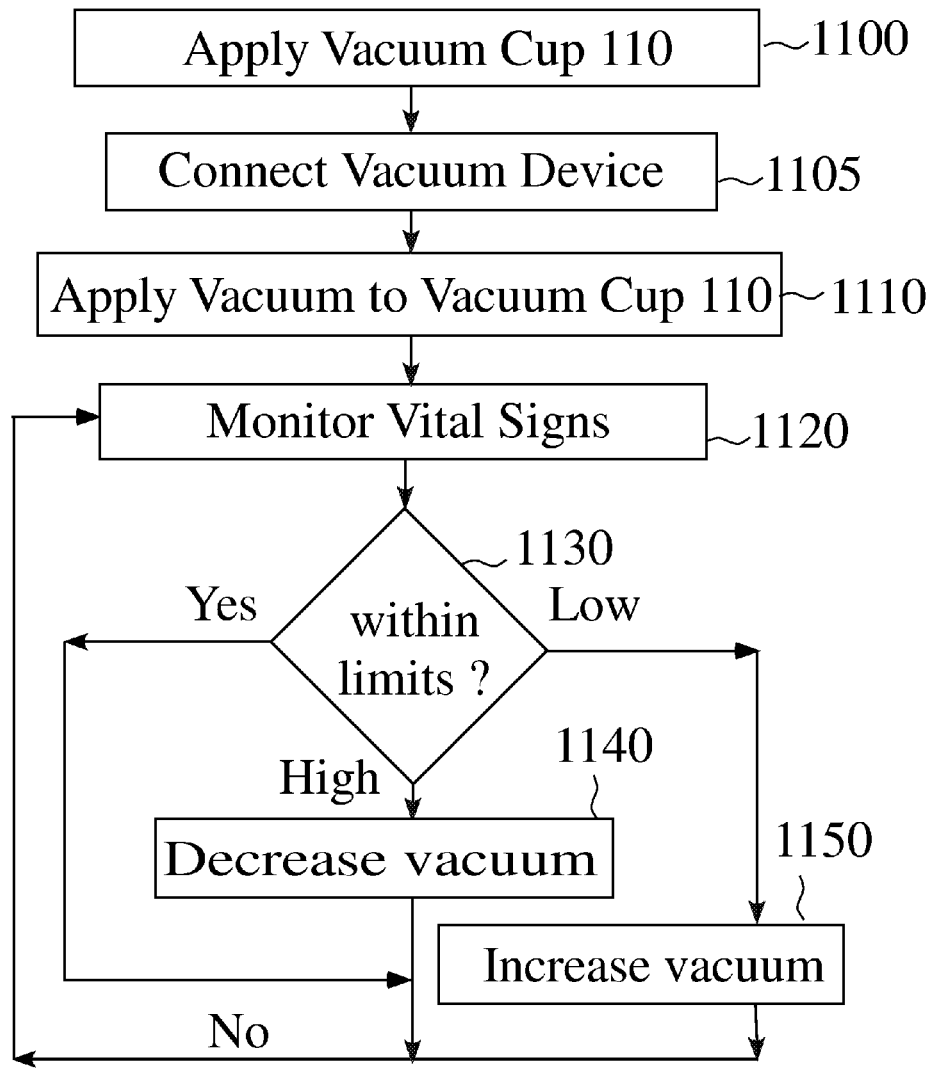
FIG. 11 is a flowchart showing the use of the vacuum cup in a procedure in accordance with an embodiment of the invention.

In an embodiment of the invention, the vacuum cup can be applied and the vital signs of a patient can be monitored and the vacuum applied to the vacuum cup adjusted based on the patients vital signs. As outlined in the flow diagram in FIG. 11, the vacuum cup 110 is first applied 1100. Next, the vacuum device for applying a vacuum to the vacuum cup 110 is connected 1105. The vacuum device is then turned on or otherwise activated to apply a vacuum to the vacuum cup 110 at 1110. The vital signs of the patient are monitored initially 1120 and then monitored at regular intervals for signs of deterioration or other untoward signs 1130. If the vital signs are within limits no adjustment of the vacuum is required. If the trauma site 560 is still bleeding the vacuum can be increased 1150. If the tissue 550 is showing discoloration then the vacuum can be decreased 1140.

A kit for use with the vacuum cup 110 further comprises a material to one or both identify the wound and wipe blood away from the wound. A nociceptive can be incorporated as a therapeutic agent. A nociceptive such as Novocain which has vasoconstrictive activity can be incorporated into the material used to wipe the trauma site and into the vacuum cup base 240 to reduce sensitization and bleeding in the periphery allowing an improved vacuum seal of the vacuum cup 110. After the wound site(s) are identified the integral suction and vacuum device is applied to the wound and activated to treat the wound and/or to stop or minimize bleeding of a wound. U.S. Pat. Nos. 5,196,196 and 5,112,608 to Scott et al., which are explicitly incorporated by reference in their entireties, describe a pressure sensitive adhesive strip for adhering the dressing to a surface surrounding the wound and administering a therapeutic agent protease nexin-I.

Application of the vacuum cup 110 at a tissue site 555 which is bleeding internally or externally 566, to apply a constant vacuum, i.e., an applied vacuum that compensates for the changed clotting behavior of the wound with time, can allow enhanced clotting and cessation of the bleeding from the site. Application of the vacuum cup 110 constricts the tissue 555 at the margin of the trauma site 566 into/toward the site. As a result, the margin collapses, allowing pooling of blood and/or clotting factors which aids in clotting and cessation of blood flow. The trauma site 566 can be one or more of a subcutaneous hematoma, an incision made by the surgeon, a site of removal of tissue by the surgeon, a site of removal of an organ made by the surgeon, one or more puncture holes being treated by the surgeon or one or more laceration sites being treated by the surgeon. Treating the wound can include stopping the blood flow from a site, reducing the blood from a site, assisting in the arrest of the flow of blood to a site, stopping the blood flow to a subcutaneous hematoma, reducing the blood flow to a subcutaneous hematoma, or assisting in the arrest of the flow of blood to a subcutaneous hematoma limiting its size and scope. Maintenance of the vacuum cup 110 on the bleeding site will ultimately more actively collapse the wound. Accordingly, the vacuum cup 110 can be utilized as a tamponade for bleeding tissue. Under these circumstances, a vacuum cup 110 can be positioned over the trauma site 566 and sufficient vacuum applied to squeeze the tissue surrounding the site and transmits pressure on the periphery of the site, closing the aperture of the trauma to either slow or completely stop the bleeding.

In experiments with an animal model or simulations with human tissue it was observed that "pop off" detachments were significantly minimized with the vacuum cup 110. If traction force exceeds the pressure under the vacuum cup 110 (the attachment force), the vacuum cup 110 base vacuum cup 240 furthest from the traction point will lift and separate from the tissue 555, causing vacuum leakage leading the cup 110 to "pop off". Essentially, when that equilibrium is reached and the two pressures equilibrate, there is a slow leak. Unexpectedly, it was found that the applied vacuum, by deforming the cup 110, moves the drug delivery surface 312 towards the tissue 555. In another unexpected result, it was found that the applied vacuum creates axial pressure 677 and radial pull 675 against the affected trauma site 566 tissue 555 moving the tissue 555 towards the drug delivery surface 312.

In various embodiments of the present invention, physical processes can be used to one or both heat and cool the surrounding tissue. In an embodiment of the present invention, a thermoelectric generator can form a part of the vacuum cup such that the surface of the generator will contact and encircle the affected tissue. The thermoelectric generator can act as a temperature pump to either heat or cool the contacting tissue. The generator can be constructed of flexible thin-film ceramic, metal or other semiconductor materials used to generate heat, or can be a device utilizing the Peltier effect to cool or heat the contacted tissue. A thermostatic safety switch can be attached to the thermoelectric generator to regulate the temperature of the generator and to act as an electrical safety cut-off should the temperature exceed desired or safe limits. A wired connection to the thermoelectric generator can be provided with an electrical connector for the attachment of an external power source.

Figure 13:
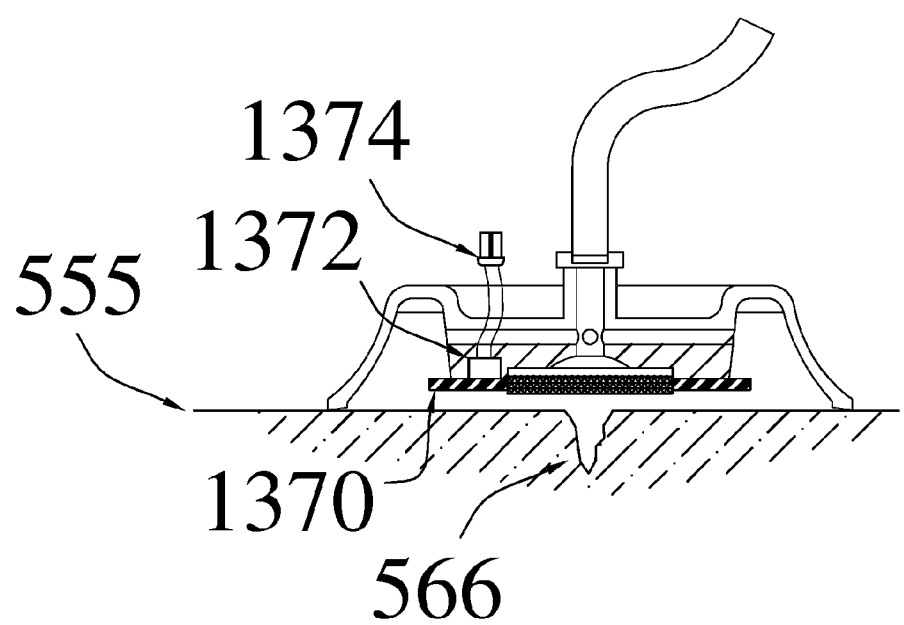
FIG. 13 is a schematic drawing of a temperature pump with a thermoelectric generator disc which encircles the trauma site incorporated into a vacuum cup, in accordance with an embodiment of the invention.

In an embodiment of the present invention, a temperature pump can be used to raise the temperature of the surrounding tissue (see FIG. 13). In FIG. 13, a thermoelectric generator disc 1370 is shown which encircles the trauma site 566 and that can heat or cool the surrounding tissue 555; a thermostatic safety switch 1372 and an electrical connector 1374 to supply power to the thermoelectric generator are also shown. In an embodiment of the present invention, the tissue can be heated with conduction of heat from a heat sink. In an embodiment of the present invention, the therapeutic agent and the vacuum can be applied with heating of the surrounding tissue to vasodilate. In an embodiment of the present invention, the therapeutic agent and the vacuum can be applied with cooling of the surrounding tissue to vasoconstrict. In an embodiment of the present invention, by controlling the blood flow through applying heating the healing process can be improved. In an alternative embodiment of the present invention, by controlling the blood flow through applying cooling the healing process can be improved. In another embodiment of the present invention, by controlling the blood flow through applying both heating and cooling to the surrounding tissue the healing process can be improved. In an embodiment of the present invention, by alternatively applying heating and then cooling the healing process can be improved.

In an embodiment of the present invention, chemical agents undergoing physical or chemical processes can be used to one or both heat and cool the surrounding tissue. release or absorption of heat can occur when a substance undergoes enthalpy of solvation, enthalpy of a chemical reaction or a phase change. A liquid to gas (liquid-gas) phase changes can have a higher heat of transformation than a solid to liquid (solid-liquid) transitions. The phase change from solid to liquid of some Phase Change Material (PCM) can be suitable for activating a temperature pump.

Agents for Activating a Temperature Pump

In various embodiments of the present invention, hydration materials can be used to cool and/or heat the surrounding tissue. In various embodiments of the present invention, reactive materials can be used to cool and/or heat the surrounding tissue. In various embodiments of the present invention, PCMs can be used to cool and/or heat the surrounding tissue and to recycle for an unlimited number of cycles within a temperature range. There are numerous PCMs available in the temperature range from −5° C. up to 40° C. that can be useful, within several in the range of 20° C. to 30° C. Two or more PCMs with different heating/cooling characteristics can also be used simultaneously. As PCMs can perform in small containers, a container can be divided into cells. The cells can be shallow to reduce the static head based on the principle of shallow container geometry.

Both organic PCMs and inorganic PCMs can be used in their pure form, combined or formulated with other substances to expand their usefulness. Common organic PCMs include paraffin waxes, 2,2-dimethyl-n-docosane ($C_{24}H_{50}$), trimyristin, (($C_{13}H_{27}COO)_3C_3H_3$), 1,3-methyl pentacosane ($C_{26}H_{54}$), other polyethylene waxes, ethylene-bis-stearamide, N,N-ethylene-bis-stearamide, which can be used alone or in mixtures thereof. Common inorganic PCMs include anhydrous sodium acetate, sodium acetate solutions, hydrated salts including sodium hydrogen phosphate dodecahydrate ($Na_2HPO_4.12H_2O$), sodium sulfate decahydrate ($Na_2SO_4.10H_2O$), ferric chloride hexahydrate ($FeCl_3.6H_2O$). Some of these mixtures can have melting temperatures below approximately 5° C. to approximately −23° C. More details can be found in U.S. Pat. No. 4,719,028, the contents of which are hereby expressly incorporated by reference in its entirety.

In an embodiment of the invention, PCMs suitable for keeping tissue cool can be solids at ambient temperature, having melting points between approximately 30° C. and approximately 50° C. Further, eutectic or near eutectic mixtures can be formed. In an embodiment of the invention, PCMs suitable for keeping tissue cool can be solids at ambient temperature, having melting points between approximately 35° C. and approximately 45° C. In general, a PCM with a higher specific heat can be advantageous. In an embodiment of the invention, PCMs have a specific heat of at least approximately 1.5-1.9.

In an embodiment of the invention, PCMs can be used to control the climate in the air surrounding the tissue. For each application, a material, a mixture of materials or a formulated material having the desired melting temperature range in the desired operating temperature range can be chosen along with other desirable properties. In an embodiment of the invention, PCMs are combined with hygroscopic substances to control the humidity. Examples of hygroscopic materials include calcium chloride, zinc chloride, potassium hydroxide, sodium hydroxide, sodium chloride, sodium iodide, and anhydrous copper sulfate.

In addition to containment of PCMs as previously discussed, encapsulation of PCMs can also be possible, not only for containment, but for increased flexibility and property improvement. For example, micro-encapsulation can allow PCMs to be incorporated into the vacuum cup construction materials. Micro-encapsulated PCMs includes coating a microscopic sized PCM with a protective coating. In this form, inorganic PCMs can be transformed into material that can be exposed to air or water, or be transformed from being hygroscopic to non-hygroscopic. Molecular-encapsulation is another technology that can enclose a very high concentration of PCM within a polymer compound. Molecular-encapsulation allows drilling and cutting through the material without any PCM leakage.

Some of the PCMs mentioned above can be recyclable in that they can undergo phase changes for an almost infinite number of times. Others can be more like endothermic agents and thus can have a limited life cycle unless handled under a controlled environment. These endothermic agents can lose their effectiveness as a phase change material even when handled under a controlled environment. In an embodiment of the present invention, even the limited life cycle PCM can be useful for cargo containers.

Figure 14:
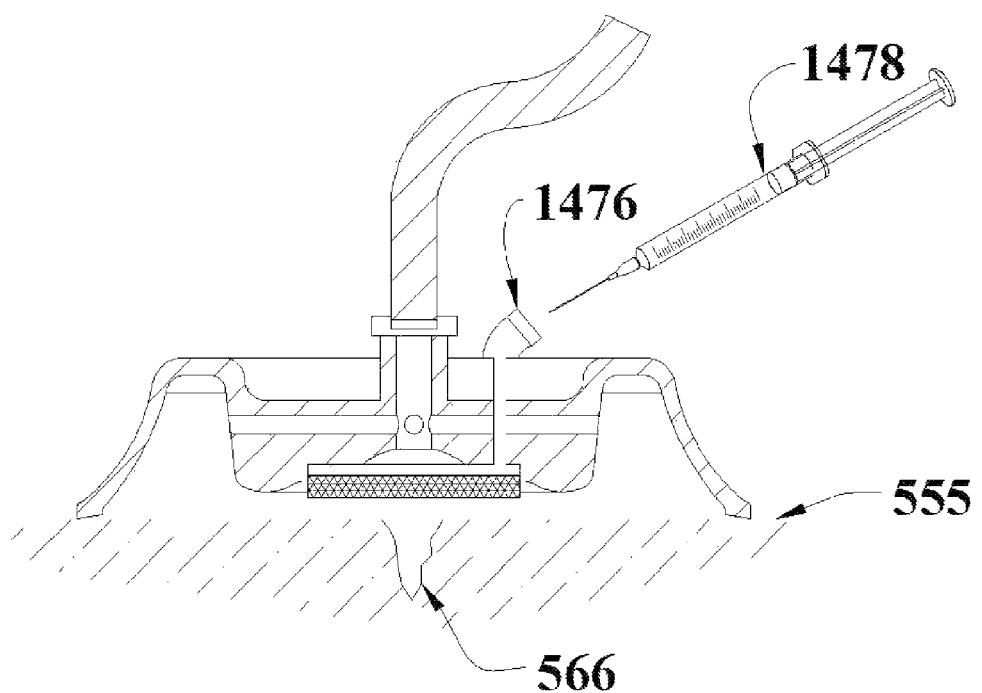
FIG. 14 is a schematic drawing of a hypodermic needle delivering an agent through the an infusion port, vernacular and rubber septum in the vacuum cup, in accordance with an embodiment of the invention.

In an embodiment of the present invention, a therapeutic agent can be infused to the wound site 566 and or the tissue surrounding the wound site 555 using a hypodermic needle 1478 through an infusion port, vernacular: rubber septum 1476 (see FIG. 14). In alternative embodiments of the present invention, manual or automatic pumps or similar devices can be used to deliver agents to the wound site. In various embodiments of the present invention, the agent delivery can be one-shot or continuous infusion.

Figure 15:
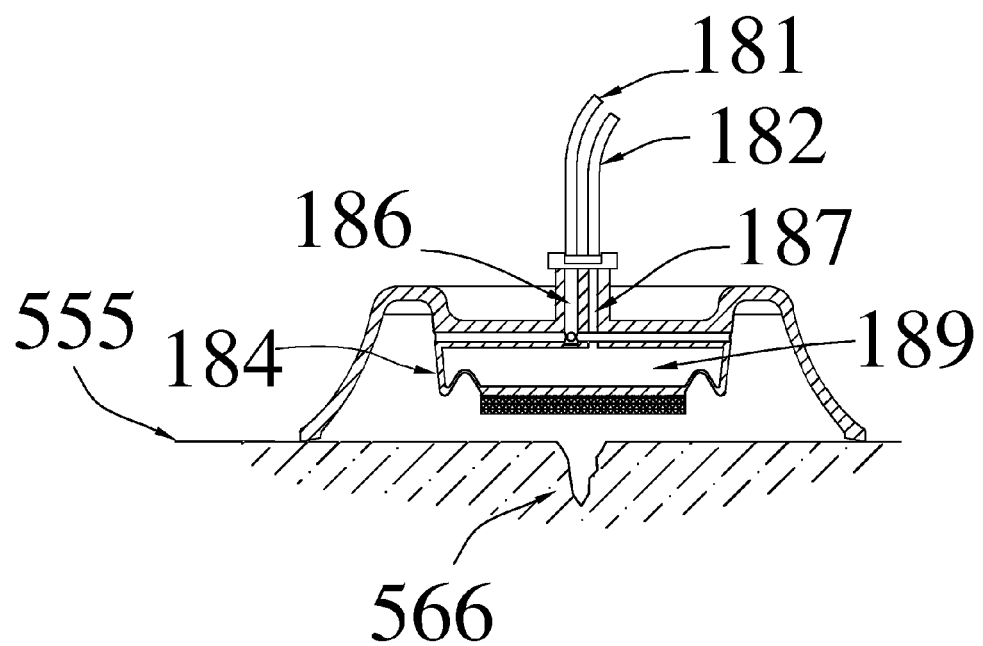
FIG. 15 is a schematic drawing of a device to apply pressure to a region within the vacuum cup, in accordance with an embodiment of the invention.
Figure 16:
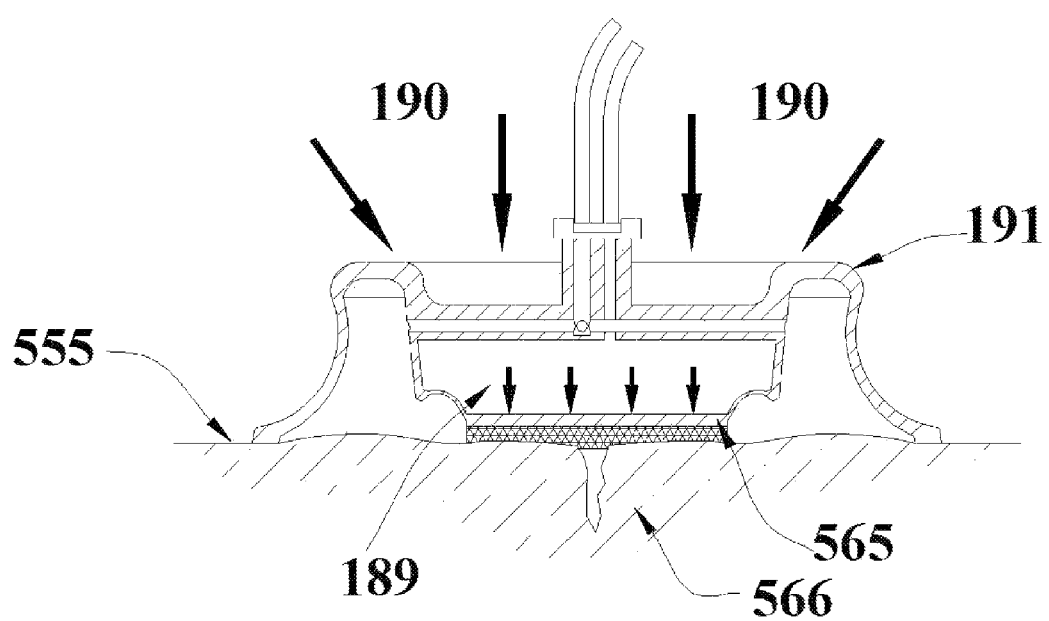
FIG. 16 is a schematic drawing of the device in FIG. 15 to apply pressure to a region within the vacuum cup, in accordance with an embodiment of the invention.

In an embodiment of the present invention, both positive and negative pressure can be applied within the cup to the surrounding tissue to improve the healing process (see FIG. 15 and FIG. 16). In this embodiment the cup utilizes both positive and negative pressure sources provided at connection ports which includes both vacuum ports 181 and positive pressure ports 182. An expandable chamber 184 which may be in a balloon or piston configuration constructed such that the expansion surface is directed towards the base of the cup to ultimately contact the tissue surface 555. Vacuum pressure is supplied by integral channels 186 to the interior of the cup to effect the previously described controlled collapse and subsequent attachment of the cup to the affected tissue surface. The desired vacuum pressure is maintained at the connection port 181 prior to the application of pressure to the positive pressure port 182. The atmospheric pressure is shown in FIG. 16 as 190. Positive pressure is provided by a channel 187 to the interior 189 of the expansion chamber 184 to expand its dimensional configuration in a controlled downward direction. The unexpected result is that the 'per square inch pressure' at 189 directly applied to the general wound location 565 can exceed the ambient surface 191 atmospheric pressure due to the pressure differential created by the vacuum pressure within the interior of the cup. The maximum applied pressure at the trauma site is determined by the ratio of the area of the expansion surface 565 as compared to the exterior surface area of the cup 191: where: APmax (Maximum Applied Pressure); AoC (Surface Area of Cup Exterior); AoE (Surface Area of Expansion Surface); 14.5 psi (Ambient Air Pressure) and APmax=14.5×(AoC/AoE). The resulting phenomenon provides a self-sustained compression at the wound area.

In an embodiment of the invention, a simulated vacuum cup for use in a teaching environment can include one or more of the novel features of the invention, but is not a working embodiment of the invention. That is, the simulated vacuum cup may be able to apply positive and negative pressure allow a hypodermic needle to be attached to the simulated vacuum cup without the ability to apply the agent through the hypodermic needle. This would make sense where the intention was to teach paramedics, hospital personnel, first responders and Army medics with the device in a simulated environment and working with either an animal model (e.g., porcine) or a model or dummy.

The present invention relates generally to the field of surgery and delivery of pharmaceutically active agents from a vacuum cup that can be positioned over a wound or trauma site to slow or completely stop bleeding. The device can deliver pharmaceutical agents, including those that assist: hemostasis (blood flow regulators that cause vasoconstriction), coagulators, blood clotting agents, sterilization including antibiotic agents (directed against bacterial, fungal and viral antigens), antiseptic agents, or other effective wound healing agents including antioxidants, vitamins, natural nutritional agents that supply agents that facilitate wound healing, anti-inflammatory agents including steroids and non-steroidal anti-inflammatory agents (NSAIDS), COX-2 inhibitors, anti-histamines, antipruritics, analgesics, anesthetics and antinociception.

In various embodiments of the invention, the vacuum cup can be used as a drug delivery device. The method of delivery can include coating the interior surfaces of the vacuum cup 110 with the agent, impregnating the interior surfaces of the vacuum cup 110 with the agent, applying a biofilm containing the agent to the interior surfaces of the vacuum cup 110, applying a gel containing the agent to the interior surfaces of the vacuum cup 110, applying a cloth containing the agent to the interior surfaces of the vacuum cup 110, applying a foam containing the agent to the interior surfaces of the vacuum cup 110, applying an absorbent material (such as cotton) containing the agent to the interior surfaces of the vacuum cup 110, and locating cavities containing a liquid agent in the interior of the vacuum cup 110 or a separate chamber containing an agent in the interior of the vacuum cup 110. That is, the vacuum cup for use in connection with arresting or slowing the flow of blood can serve as a receptacle for a pharmaceutically active agent.

Various therapeutic agents can be delivered via the present invention. They include many different types of agents with different uses and are discussed in the following paragraphs. An antihemorrhagic (antihaemorrhagic) agent is a substance that promotes hemostasis (stops bleeding). Antihemorrhagic agents used in medicine have various mechanisms of action. Systemic drugs work by inhibiting fibrinolysis or promoting coagulation. There are several classes of antihemorrhagic drugs. These include antifibrinolytics, vitamin K, fibrinogen, and blood coagulation factors. Locally-acting hemostatic agents work by causing vasoconstriction or promoting platelet aggregation (e.g., microfibrillar collagen, chitosan and styptics). These hemostatic agents can be embedded in a dressing. Microfibrillar collagen hemostat (MCH) is a topical agent composed of resorbable microfibrillar collagen. It attracts platelets and allows for the formation of a blood clot when it comes into contact with blood. The cup presses the MCH against a bleeding site, and the collagen attracts and helps with the clotting process to eventually stop bleeding. Chitosan hemostats are topical agents composed of chitosan and its salts. Chitosan bonds with platelets and red blood cells to form a gel-like clot which seals a bleeding vessel. Unlike other hemostat technologies its action does not require the normal hemostatic pathway and therefore continues to function even when anticoagulants like heparin are present. Hemostatic chemicals use Chitosan in commercial products such as roll gauzes, and granular powders. Zeolite, for example is used in QuikClot, a dressing. Styptics (anhydrous aluminum sulfate, potassium alum or titanium dioxide) are a specific type of antihemorrhagic agent that work by contracting tissue causing blood vessels to contract at the site of the wound and thereby to seal the damaged blood vessels.

Vasoconstrictors constrict vessels supplying blood flow. DDAVP (1-deamino-8-D-arginine vasopressin or desmopressin) a derivative of the diuretic hormone is used to treat patients with factor VIII, von Willebrand bleeding disorders, hemophilia, chronic kidney disease, chronic liver disease and patients undergoing operations where large blood loss and/or transfusions are required. Other adrenergic agents exhibit vasoconstrictive action including adrenaline.

A topical anesthetic is a local anesthetic that can be used to numb the surface of a body part. They can be used to numb any area of the skin as well as the front of the eyeball, the inside of the nose, ear or throat, the anus and the genital area. Topical anesthetics are available in creams, ointments, aerosols, sprays, lotions, and jellies. Examples include benzocaine, butamben, dibucaine, lidocaine, oxybuprocaine, pramoxine, proparacaine, proxymetacaine, and tetracaine (also named amethocaine). Some topical anesthetics are, for example, oxybuprocaine, benzocaine and lidocaine. For neuropathic pain, centrally acting substances like anticonvulsants (pregabalin, gabapentin and carbamazepine) or antidepressants such as SSRIs (selective serotonin reuptake inhibitors) or the tricyclic antidepressant amitriptyline can be used.

Local delivery of analgesia agents to wound sites can reduce pre- and postoperative pain, while limiting systemic side effects of analgesia. Additional benefits include reduced need for oral narcotics, decreased incidence of breakthrough pain, and faster return to normal activities. Drug delivery can be regulated through monitoring of the agent delivered. Analgesics include ibuprofen, diclofenac, ropivicaine, bupivacaine or capsaicin. In an embodiment of the invention, the analgesic can be delivered with a hyperdermic needle dispensing the analgesic into a sponge. In an embodiment of the invention, a gel containing a specific amount of analgesic can be used to topically introduce the analgesic. In an embodiment of the invention, an anesthetic such as lidocaine can also be used to numb areas for medical procedures. In an embodiment of the invention, an anesthetic such as lidocaine can be present within the inset 241 surrounding the bead 242 on the edge of cup lip and released when the cup is placed on the patient (as shown in FIGS. 5 and 6). A protective strip can be used to isolate the anesthetic from the atmosphere while the cup is stored. Removing the protective strip from the bead 242 and applying the cup to the patient applies the anesthetic to the area surrounding the wound 566 desensitizing the area 555. An analgesic agent can then be introduced with little discomfort to the patient. In an embodiment of the invention, the protective strip can be composed in part of PVA, PVP and/or PDMV. In an embodiment of the invention, moisture from the tissue 555 allows for hydrolysis of the water soluble polymers allowing time release of the active agent. In an embodiment of the invention, introduction of an efflorescent material can be used to hydrolyse the water soluble polymer and trigger the release of the active agent.

Topical antipruritics are in the form of creams. The active ingredients usually belong to the following classes: antihistamines such as diphenhydramine (Benadryl); corticosteroids such as hydrocortisone; local anesthetics such as benzocaine topical cream (Lanacaine); counter-irritantssuch as mint oil, menthol, or camphor; SSRIs (selective serotonin reuptake inhibitors); mirtazapine which has antipruritic effects due to its strong antagonism of the H1 receptor; calamine lotioncontaining zinc oxide and iron(III) oxide; paste of sodium bicarbonate; and ammonium hydroxide.

Wound healing is the complex process of regenerating dermal and epidermal tissue after skin injury. Matrix Metalloproteinases (MMPs), which can degrade proteins, are essential in breaking down wounded tissues to allow for wound healing. MMPs play a key role in movement of skin cells, and can contribute to new blood vessel growth. Topical treatment with MMP-9 and MMP-13 increases the rate of wound healing compared with mammals lacking MMP-9 and/or MMP-13 which exhibit a significant delay in macroscopic wound closure and histological re-epithelialization. Wound healing can be facilitated by the application of the MMPs or inducers of the MMPs. Hormones can accelerate wound healing; examples of such hormones include estrogen, leptins, deoxyribonucleosides, recombinant genetically engineered repifermin, and recombinant human keratinocyte growth factor-2.

Antibiotics, used to treat a variety of infections, are known in the art and are numerous; some examples follow. Antibiotics include Aaminoglycosides which are active against infections caused by Gram-negative bacteria such as *Escherichia coli* and *Klebsiella* particularly *Pseudomonas aeruginosa* and are also effective against aerobic bacteria and tularemia; specific aminoglycosides include: amikacin, gentamicin, kanamycin, neomycin, netilmicin, tobramycin and paromomycin. Geldanamycin and herbimycin are anti-tumor antibiotics. Loracarbef, another antibiotic, prevents bacterial cell division by inhibiting cell wall synthesis. Carbanapems active against gram positive and gram negative bacteria include ertapenem, doripenem, imipenem/cilastatin and eropenem. Cephalosporins active against gram positive bacteria include: cefadroxil, cefazolin, cefalotin, efalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cephalosporins, cefepime and ceftobiprole. The glycopeptides, teicoplanin, vancomycin andtelavancin inhibit peptidoglycan synthesis. Lincoamides active against staph-, pneumo-, and streptococcal infections in penicillin-allergic patients and also in anaerobic infections include clindamycin and lincomycin. Lipopeptides active against gram positive bacterial infections include daptomycin. Macrolides, active against streptococcal infections, syphilis, upper respiratory tract infections and lower respiratory tract infections include: azithromycin, clarithromycin, dirithromycin, erythromycin, roxithromycin, troleandomycin, telithromycin and spectinomycin. Aztreonam, a monobactams, disrupts the synthesis of the peptidoglycan layer of bacterial cell walls. Nitrofurans active against bacterial or protozoal diarrhea or enteritis include Furazolidone and itrofurantoin. Penicillins active against a wide spectrum of bacterial infections include: amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin and ticarcillin. Polypeptides active against gram negative bacterial infections in the eye, ear or bladder include: bacitracin, ceropin A, cecropin B, colistin and polymyxin B. Quinolones active against infections including urinary tract infections (UTI), bacterial prostatitis, community-acquired pneumonia, bacterial diarrhea, mycoplasmal infections, and gonorrhea include: ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin and temafloxacin. Sulfonamides active against infections including UTI include: sulfonamidochrysoidine (archaic), sulfadiazine, sulfamethizole, sulfamethoxazole, sulfanilimide (archaic), sulfasalazine, sulfisoxazole, trimethoprim and trimethoprim-sulfamethoxazole. Sulfacetamide is used for eye infections. Mafenide and silver sulfadiazine can be used topically for burns. Tetracycline antibiotics active against syphilis, chlamydial infections, Lyme disease, mycoplasmal infections, acne rickettsial infections and malaria include: demeclocycline, doxycycline, minocycline, oxytetracycline and tetracycline. Antibiotics directed against mycobacteria include: clofazimine, dapsone, capreomycin, cycloserine, ethambutol, isoniazid, pyrazinamide, rifampin, rifabutin, rifapentine and streptomycin. Ethionamide inhibits peptide synthesis.

Epigallocatechin gallate (EGCG), is the most abundant catechin in tea. EGCG is a potent antioxidant and is found in green tea, but not black tea, as EGCG is converted into the arubigins in black teas. EGCG is used in many dietary supplements. EGCG can have therapeutic properties for many disorders including cancer. However, some studies indicate it can have deleterious effects in binding to and inactivating prescription therapeutic compounds.

Citrate is the conjugate base of citric acid, $(C_3H_5O(COO)_3^{3-})$, where in solution intermediate ions hydrogen citrate ion $(HC_6H_5O_7^{2-})$ and di-hydrogen citrate ion $(H_2C_6H_5O_7^{-})$ also exist. Citrate is an intermediate in the 'Krebs' tri-carboxylic acid cycle (TCA). Pyruvate dehydrogenase complex forms acetyl coenzyme A, from pyruvate and the cofactors, thiamine pyrophosphate, lipoamide, flavin adenine di-nucleotide, nicotinamide adenine dinucleotide, and coenzyme A. Citrate synthase catalyzes the condensation of oxaloacetate with acetyl coenzyme A to form citrate. Citrate also reacts in the TCA cycle via aconitate hydratase leading to the regeneration of oxaloacetate, which can combine with another molecule of acetyl coenzyme A. Citrate is also involved in fatty acid synthesis after being transported into the cytoplasm and converted to acetyl coenzyme A. Acetyl coenzyme A carboxylase is an enzyme which is regulated by citrate and converts acetyl coenzyme A into malonyl coenzyme A. High concentrations of cytosolic citrate can also inhibit glycolysis through its actions on phospho-fructokinase. Citrate can also be used to buffer the pH of solutions and some forms of citrate can act as chelating agents. For example, tri-sodium citrate can chelate calcium ions to inhibit coagulation.

Citric bio-flavonoids are a class of poly-phenolic plant secondary metabolites, containing a ketone group. They are known for their antioxidant activity and health-modulating effects. However, other researchers indicate that inside the human body, bio-flavonoids themselves are of little or no direct antioxidant value because the bio-flavonoids are poorly absorbed (less than 5%), with most of what is absorbed being quickly metabolized and excreted as the body sees them as foreign compounds and is trying to get rid of them. The citrus bio-flavonoids include hesperidin (a glycoside of the flavanone hesperetin), quercitrin, rutin (two glycosides of the flavonol quercetin), and the flavone tangeritin. Quercetin is the aglycone form of a number of other flavonoid glycosides, such as rutin and quercitrin, found in citrus fruit, buckwheat and onions. Quercetin forms the glycosides quercitrin and rutin together with rhamnose and rutinose, respectively. Grape skins contain significant amounts of bio-flavonoids and as a result both red and white wine contain bio-flavonoids. Since red wine is produced by fermentation in the presence of the grape skins, red wine has been observed to contain higher levels of bio-flavonoids. Contrasting views on the health benefits of bio-flavonoids and other poly-phenolics such as resveratrol have been presented.

Flavonoids, sulphated carbohydrates, or terpenoids have been suspected to be the active anti-angiogenic components of plant products. Catechins and poly-phenols have been suggested to show anti-cancer activity. Silymarin, a naturally occurring bioflavonoid, has also been suggested to exhibit anti-cancer effects. It has been proposed that bio-flavonoids can contribute to the preventive effect of a plant-based diet on chronic diseases. Edible berries have been suggested to possess a broad spectrum of important therapeutic and chemopreventive agents. Studies suggest that the anthocyanins found in berries reduce oxidative stress and assist with neuronal and cognitive functions.

Vitamin E is a generic term for a family of alpha, beta, gamma and delta-tocopherols and corresponding four tocotrienols. Alpha tocopherol has the highest bioavailability and has been studied more thoroughly. Alpha tocopherol is an essential vitamin, important in the formation of red blood cells. Alpha tocopherol is also used by the body to utilize vitamin K. Alpha tocopherol is a fat-soluble antioxidant that has been reported to stops the production of reactive oxygen species formed when fat undergoes oxidation.

Glucosamine is an amino sugar and a prominent precursor in the biochemical synthesis of glycosylated proteins and lipids. Glucosamine is part of the structure of the polysaccharides chitosan and chitin, which compose the exoskeletons of crustaceans and other arthropods. Glucosamine is also present in the cell walls in fungi and many higher organisms. Chondroitin sulfate is a sulfated glycosaminoglycan composed of a chain of alternating N-acetylgalactosamine and glucuronic acid sugars found attached to proteins as part of a proteoglycan. Hyaluronan is a polysaccharide consisting of alternative residues of D-glucuronic acid and N-acetylglucosamine, found in the extracellular space. Hyaluron is translocated out of the cell during biosynthesis and is found on the inner surface of the cell membrane. Hyaluron confers upon tissues the ability to resist compression by providing a counteracting swelling force. Sialic acids include N-acetylneuraminic acid and N- and O-substituted derivatives of neuraminic acid. Sialic acids are found widely distributed in animal tissues.

In various embodiments of the invention, the therapeutic agent can be one that assists in arresting or slowing the flow of blood. A large number of such agents are known. For example, Floseal™ is available from Baxter, which consists of bovine thrombin plus cross-linked gelatin granules. A number of different therapeutic agents can be used in conjunction with the device of the present invention. These include, but are not limited to fibrin sealants, a gelatin sponge or Gelfoam®, oxidized regenerated cellulose such as is sold under the trade names Surgicel or Oxycel, microfibrillar collagen commercially known as Avitene®, and collagen sponges available under a wide variety of different commercial forms. U.S. Pat. No. 4,997,753 to R. Dean et al.; U.S. Pat. No. 4,971,954 to B. Brodsky et al. and U.S. Pat. No. 4,970,298 to F. Silver et al., which are all explicitly incorporated by reference in their entireties, describe modified collagen useful for immobilizing a therapeutic agent. Additional hemostatic agents are also known. These include completely autologous fibrin sealants and target platelet gels in which platelets are purified with plasma and the patient's own serum are combined with thrombin. There are also completely synthetic agents, which are made from polyethylene glycol gels that when combined make a completely synthetic hydrogel. U.S. Pat. Nos. 6,911,496; 6,534,591; 6,166,130; 5,874,500 and 5,643,464 to W. Rhee et al., which are explicitly incorporated by reference in their entireties, describe synthetic gels for administering therapeutic agents. C1-inhibitor is a serine protease inhibitor whose deficiency has been associated with hereditary angioedema. U.S. Pat. No. 7,837,992 to V. Gurewich et al., which is explicitly incorporated by reference in its entirety, describes the use of a mutant prourokinase plasminogen activator and C-1 inhibitor for reducing bleeding while preventing fibrinogen degradation. Bovine serum plus albumin plus glutaraldehyde can also be used. N-acetyl glucosamine can be derived from seaweed, and can also serve as a hemostatic agent.

Cytokines, interferon, monoclonal antibodies, immune modulators in the class of imiquimod (Meda AB) and their isomers. Imiquimod activates immune cells through the toll-like receptor 7 to secrete cytokines including interferon-$\alpha$, interleukin-6, tumor necrosis factor-$\alpha$, natural killer cells, macrophages and B-lymphocytes, and activates other antiproliferative effects via activation of the opioid growth factor receptor. Other immune modulators include Calcineurin inhibitors which include specific T-cell inhibitors such as cyclosporine and tacrolimus. Cyclosporine binds to the cytosolic protein cyclophilin of lymphocytes, especially T cells. Tacrolimus acts to inhibit T-cell activation via a down regulation of interleukin-2 Cyclosporine also blocks the formation of the mitochondrial permeability transition pore, and can thereby reduce the damage associated with head injury and neurodegenerative diseases.

Antiproliferative drugs include Azathioprine, Cyclophosphamide, Methotrexate, Chlorambucil, Mycophenolate mofetil, Glucocorticoids (Prednisolone), Antibodies Muromonab CD3, Antithymocyte globin or ATG, Rho (D) immuneglobin and Efalizumab); and Immunostimulant agents. Antiproliferative drugs can stimulate the immune system to fight against immunodeficiencies like AIDS, infections and cancers. Antiproliferative drugs include levamisole which is an antihelmintic drug that also restores functions of B lymphocytes, T lymphocytes, monocytes and macrophages and has been used to treat colon cancer along with 5-FU; Thalidomide which has been used to treat Erythema nodosum leprosum by providing an anti-inflammatory effect, to treat multiple myeloma by providing an anti-angiogenesis effect, and to treat rheumatoid arthritis by providing an anti TNF effect; BCG which has been used to treat carcinoma in the bladder; recombinant cytokines including Interferons which have been used to treat tumors and chronic hepatitis B and C; Interleukin 2 (aldeslukin) which has been used to treat renal cell carcinoma and melanoma; and Tolerogens which has been used to induce tolerance and make the tissue non-responsive to antigens, including Human leukocyte antigen which induces tolerance through blood and recombinant fusion protein molecules such as anti CD50 MAB and anti CD56 MAB which block activation of T lymphocytes via CD28 (on T lymphocytes) and CD80 and CD86 on agonist presenting cell.

Antiseizure agents, sleep aids, anti-ulcer agents for the gastrointestinal tract, and agents for the treatment of patients suffering from type I or type II diabetes can be "adjunctive agents" delivered systemically via the vascular or microvascular system "exposed" during a vascular injury or post injury that creates a wound port of entry. In appropriate patients requiring adjunctive agents, the delivery of the agent through the wound can be affected. In an embodiment of the invention, RFID (Radio Frequency Identification) tags are used to identify the requirements of the patient and correlate with the appropriateness of the equipment and agents used to treat the patient.

The vacuum cup can also be configured to deliver pharmaceutical agents other than those associated with hemostasis. For example, antibiotic agents or agents that promote the healing of wounds can also be delivered. These additional agents can be provided either on their own or in conjunction with hemostatic agents.

In an embodiment of the invention, the pharmaceutically active agents to be delivered with the vacuum cup can be delivered in a number of different manners. The agents can be provided in the form of a cream or a gel introduced inside the cup. Alternatively, the agent can be sprayed into or under the cup before the vacuum is applied. The agent can be received in an aerosol can and the spray produced from the aerosol can. In an embodiment of the invention, the agent can be in liquid, gas, or solid in form. In an embodiment of the invention, the agent can be attached or impregnated into a sponge or cotton wad. In an alternative embodiment of the invention, the pharmaceutically active agent can also be incorporated directly onto the material of the cup and slowly released during use. The pharmaceutically active agent can be a gel that is present within the inset surrounding the bead on the edge of cup lip and slowly released during use. A protective strip can isolate the agent from the atmosphere while the cup is stored. Removing the protective strip from the bead and applying the cup to the patient such that the bead contacts the area surrounding the wound allows the agent to be introduced into and around the wound.

The pharmaceutically active agents can be delivered via a platform located inside the cup. As noted above, many of the hemostatic agents can be in the form of cellulose or a sponge. These can be provided directly as a platform within the cup. Additionally, other agents can be delivered by absorbing them into a pharmacologically inactive cellulose or sponge. A sponge can advantageously also serve to apply pressure to the wound or targeted tissue. Another advantage of a sponge or cellulose material is that it can also serve as a filter to prevent materials, such as pharmaceutically active gel, from being sucked into the vacuum line. Any of the large number of filter materials known can be adapted to absorb pharmaceutically active agents for the purpose of the present invention.

In an embodiment of the invention, a system for administering a medicament comprises a vacuum cup 110, a membrane with the medicament, a vacuum device for applying a vacuum to the suction device, wherein one or all of the vacuum cup 110, the membrane with the medicament and the vacuum device include a RFID tag. In an embodiment of the invention, a RFID reader can read the one or more RFID tags which function as input modules for selecting parameters for use with the vacuum cup. The input modules select parameters based at least in part on the vacuum cup 110 selected, a sensor for monitoring the vacuum applied by the vacuum device to the vacuum cup 110, and a processor for comparing the vacuum applied to the vacuum cup 110. The selected parameters act to automatically activate the vacuum device to increase the vacuum to the vacuum cup 110 when the comparison indicates an increased vacuum is required.

In an embodiment of the invention, the RFID tag present on each vacuum cup 110 can be used to detect the presence and/or location of vacuum cups that have been placed within a body cavity. In an alternative embodiment of the invention, a radio wave visible tag present on each vacuum cup 110 can be used to detect the presence and/or location of vacuum cups that have been placed within a body cavity. Using these tags, the processor associated with vacuum device can track the number and type of vacuum cups used during surgery to insure correct installation, use and retrieval of the cups 110 pre, during and post surgery.

In an embodiment of the invention, a system for a first responder to administer a medicament in a mammal comprises an integral membrane/suction and vacuum device for administering a medicament to a tissue. The integral membrane/suction and vacuum device includes a switch to activate the integral membrane/suction and vacuum device; a membrane containing a medicament; a suction cup 110; a relief valve; a vacuum pump, wherein the vacuum pump generates a vacuum at the suction cup; a sensor for monitoring the vacuum at the suction cup; and a processor. The processor compares the vacuum applied to the suction cup 110 with the selected parameters and automatically activates the vacuum pump to increase the vacuum to the suction cup 110 when the comparison indicates an increased vacuum is required for one or both of controlling homeostasis and administering the medicament. Application of the suction cup 110 and the vacuum for administering a medicament to a tissue attaches the integral membrane/suction and vacuum device to the mammal such that movement of the mammal does not detach the integral membrane/suction and vacuum device.

In an embodiment of the invention, a system for adjusting and monitoring the amount of medicament administered through a vacuum cup 110 during a surgical procedure, comprises a vacuum device for applying a vacuum to the vacuum cup 110. The vacuum device includes an input module for selecting parameters for use with the vacuum cup 110, wherein the input module selects parameters based at least in part on the membrane and medicament selected; the vacuum cup 110 selected; a sensor for monitoring the vacuum applied by the vacuum device to the vacuum cup 110; and a processor for comparing the vacuum applied to the vacuum cup 110 with the selected parameters and automatically activating the vacuum device to increase the vacuum to the vacuum cup 110 when the comparison indicates an increased vacuum is required. In an embodiment of the invention, the system also comprises a device to monitor the subject's vital signs including the subject's pulse, heart rate, breathing, temperature, and perspiration, wherein the subject's vital signs are used to adjust the vacuum device parameters.

In an embodiment of the present invention, wireless communications circuitry can provide modulated waveform signals in either the infrared (IR) or radio frequency (RF) signal range. In an embodiment of the invention, the wireless communications circuitry can provide RF inputs/outputs. The modulated signals can be transmitted using any typical small computer Ethernet system with a WiFi standard device such as EIA-802.11G, Bluetooth® methodology or discrete signaling utilizing a non-linear code encryption algorithm for secure control. The wireless communications circuitry can be controlled through an interface with the vacuum cup 110 processor circuitry to provide remote control and data transfer between the vacuum cup 110 and peripheral devices such as: remote control units (pushbuttons, foot switches), personal computers, printers or other portable computing devices such as personal digital assistants (PDA), mass storage devices, or digital telecom devices such as cellular telephones.

In an embodiment of the present invention, a wireless control unit can be a small form factor self-contained RF transmitter with an integral storage battery power source. In an embodiment of the present invention, the wireless control unit can be wirelessly connected to the vacuum cup 110 utilizing the wireless communications circuitry with discrete signaling utilizing a non-linear code encryption algorithm for secure control. In an embodiment of the present invention, the wireless control unit control mechanism can be comprised of two (2) or more mechanically actuated push-button switches with tactile surfaces allowing the operator to differentiate between the buttons and thereby allowing each button to be identified without visual verification. Tactile differentiation can be accomplished by unique button size, shape, embossed or raised symbols, or any combination of these methods. The wireless control unit can allow the vacuum cup 110 to be operated remotely. Through the actuation of a single or predefined combination of buttons, the operation of the vacuum cup 110 can be controlled. Control functions include: vacuum pump on/off, release of vacuum, real-time adjustment of regulated vacuum operating pressure and adjustment of other operating parameters as afforded by the device processor circuitry.

In another embodiment of the invention, a RFID tag can be imbedded in one or more of: the vacuum cups 110. In an embodiment of the invention, the RFID tag can be used to identify the vacuum cup and thereby determine the parameters for operation of the vacuum cup 110. In one embodiment of the invention, the RFID tag operates using an Ultra High Frequency (UHF) signal. In another embodiment of the invention, the RFID tag operates using a microwave frequency signal.

In an embodiment of the present invention, a RFID reader can be present in the vacuum cup 110 which can then read the RFID tags associated with the therapeutic agent to be dispensed. In an embodiment of the invention, the RFID reader can be positioned so that the RFID tag antenna is least affected by any conducting material. In an embodiment of the present invention, a RFID reader can be present in the vacuum device which can then read the RFID tags associated with the vacuum cup 110 and the therapeutic agent to be dispensed. In an embodiment of the invention, the RFID reader can be positioned so that the RFID tag antenna is least affected by any conducting material.

In one embodiment the RFID tag can be read only. In another embodiment, the RFID tag contains an Electrically Erasable Programmable Read-Only Memory (EPROM), which enables both read and write functions. In an embodiment of the invention, the RFID tag is passive. In another embodiment of the invention, the RFID tag is semi-passive containing a source of energy such as a battery to allow the tag to be constantly powered. In a further embodiment of the invention, the RFID tag is active, containing an internal power source, such as a battery, which can be used to power any Integrated Circuits (ICs) in the tag and generate the outgoing signal. In another embodiment, the tag has the ability to enable location sensing through a photo sensor.

In an embodiment of the invention, the system is able to monitor the type, previous use, data and condition of the vacuum cup 110. In this manner, an emergency responder, first aid medic or surgeon can choose a procedure and then the system can check that the set-up is appropriate for the procedure chosen including the vacuum cup 110 selected and the therapeutic agent to be administered.

In one embodiment of the invention, means of communication with a base station can be embedded in the vacuum cup 110. In an alternative embodiment of the invention, means of communication with a base station can be embedded in the vacuum device.

In one embodiment of the invention, the communication means utilizes one or more of a wireless local area network; a wireless wide area network; a cellular network; a satellite network; a Wi-Fi network; and a pager network. In one embodiment of the invention, a modem capable of communicating with one or more of the aforementioned networks can be embedded in the vacuum cup 110. In an alternative embodiment of the invention, a modem capable of communicating with one or more of the aforementioned networks can be embedded in the vacuum device.

In this discussion the term 'cellular modem' will be used to describe the device embedded. The term 'cellular modem' will be herein used to identify any device of comparable size capable of communicating over one or more of the aforementioned networks. In one embodiment of the invention, the cellular modem can be a Code Division Multiple Access (CDMA) modem. In an embodiment of the invention, a RFID reader and associate integrated circuit processor can be embedded together with the cellular modem in the vacuum cup 110. In such an embodiment, the RFID tags and RFID reader can be positioned to optimize the RFID read of the RFID tags from the available devices. In an alternative embodiment of the invention, a RFID reader and associate integrated circuit processor can be embedded together with the cellular modem in the vacuum device. In such an embodiment, the RFID tags and RFID reader can be positioned to optimize the RFID read of the RFID tags from the available devices.

In an embodiment of the invention, a RFID reader and a cellular modem can be positioned in the vacuum cup 110; the RFID reader can be in communication with one or more RFID readers, associated cellular modems and the RFID tags of one or more therapeutic agents located in the vacuum cup 110. In an alternative embodiment of the invention, a RFID reader and a cellular modem can be positioned in the vacuum device; the RFID reader can be in communication with one or more RFID readers, associated cellular modems and the RFID tags of one or more vacuum cups 110, and therapeutic agents located in the vacuum cups 110. Through communications with the RFID reader and associated integrated circuit processor of the plurality of vacuum cup 110, a RFID reader and associated integrated circuit processor are able to distinguish the RFID tag from a vacuum cup 110 in the vicinity based on one or more of location, strength of signal, variation of RFID tag signal with position, variation of RFID tag signal with time, and prior input data. In an embodiment of the invention, one or more antenna inserted can be used to help discriminate the location of the vacuum cup 110. In an embodiment of the invention, the RFID reader and associate processor can be in communication with the cellular modem. In an embodiment of the invention, the cellular modem can be in communication with a base station and can transmit one or more parameters selected from the group consisting of one or more RFID tag location, one or more RFID tag identification code, vacuum cup 110, therapeutic agents, vacuum device, vacuum device conditions, suction device conditions, and time stamp.

In one embodiment of the invention the RFID code uses the IEEE format and is Electronic Product Code (EPC) readable. In another embodiment of the invention the RFID code uses the UCC format and is Universal Product Code (UPC) readable. In another embodiment, the format is compatible for EPC, European Article Number (EAN) and UPC read and write functions.

In an embodiment of the invention, the vacuum device further comprises one or both visual and audio feedback that allows one or more methods of control of the vacuum applied to the vacuum cup 110, control of the vacuum device and adjustment of the vacuum device settings during the procedure.

In an embodiment of the invention, the vacuum cup 110 can be portable. In an embodiment of the invention, the vacuum cup 110 can be hand held. In an embodiment of the invention, the vacuum cup 110 can be portable and hand held.

In an embodiment of the invention, a system for adjusting and monitoring a vacuum system comprises a vacuum cup 110 for applying a vacuum to the patient, wherein the vacuum cup 110 includes an RFID tag reader, wherein the RFID tag reader can read an RFID tag on therapeutic agents loaded in the vacuum cup 110; an input module for selecting parameters for use with the vacuum cup 110, wherein the input module selects parameters based at least in part on the vacuum cup 110 selected and the therapeutic agents selected; a sensor for monitoring the vacuum applied by the vacuum device to the vacuum cup 110; and a processor for comparing the vacuum applied to the vacuum cup 110 with the selected parameters and automatically activating the vacuum device to increase the vacuum to the vacuum cup 110 when the comparison indicates an increased vacuum is required.

In an embodiment of the invention, a system for a first responder to minimize bleeding of a wound in a mammal comprises an integral suction and vacuum device for applying a vacuum to the wound. The integral suction and vacuum device includes a switch to activate the integral suction and vacuum device; a vacuum cup 110; a relief valve; a vacuum pump, wherein the vacuum pump generates a vacuum at the vacuum cup 110; a sensor for monitoring the vacuum at the vacuum cup 110; and a processor. The processor compares the vacuum applied to the vacuum cup 110 with the selected parameters and automatically activates the vacuum pump to increase the vacuum to the vacuum cup 110 when the comparison indicates an increased vacuum is required; when the comparison indicates a decreased vacuum is required, the processor one or both deactivates the vacuum pump and automatically opens the relief valve Application of the vacuum cup 110 and the vacuum to the wound attaches the integral suction and vacuum device to the mammal such that movement of the mammal does not detach the integral suction and vacuum device.

In an embodiment of the invention, the vacuum cup can be applied in any scientific, manufacturing, or industrial apparatus that requires the use of a vacuum cup 110. This can include laboratory equipment that requires vacuum assisted grasping, reactions, sampling, storage or any other clinical procedure. The manipulation of components, fluids or assemblies used in a manufacturing process, including precision handling, clean-room transport, and material transport can also be achieved using the vacuum cup 110 and the vacuum device.

Various embodiments can be implemented using a conventional general purpose or specialized digital computer(s) and/or processor(s) programmed according to the teachings of the present disclosure, as will be apparent to those skilled in the computer art. Appropriate software coding can readily be prepared by skilled programmers based on the teachings of the present disclosure, as will be apparent to those skilled in the software art. The invention can also be implemented by the preparation of integrated circuits and/or by interconnecting an appropriate network of component circuits, as will be readily apparent to those skilled in the art.

Embodiments of the present invention can include a computer readable medium, such as computer readable storage medium. The computer readable storage medium can have stored instructions which can be used to program a computer to perform any of the features present herein. The storage medium can include, but is not limited to, any type of disk including floppy disks, optical discs, DVD, CD-ROMs, micro drive, and magneto-optical disks, ROMs, RAMs, EPROMs, EEPROMs, DRAMs, flash memory or any media or device suitable for storing instructions and/or data. The present invention can include software for controlling both the hardware of a computer, such as general purpose/specialized computer(s) or microprocessor(s), and for enabling them to interact with a human user or other mechanism utilizing the results of the present invention. Such software can include, but is not limited to, device drivers, operating systems, execution environments/containers, and user applications.

Embodiments of the present invention can include a computer-implemented method for transmitting the code which can be executed at a computer to perform any of the processes of embodiments of the present invention. The transmitting can include transfer through any portion of a network such as the Internet; through wires, the atmosphere or space; or through any other type of transmission. The transmitting can include initiating a transmission of code, or causing the code to pass into any region or country from another region or country. A transmission to a user can include any transmission received by the user in any region or country, regardless of the location from which the transmission is sent.

Embodiments of the present invention can include providing code for implementing processes of the present invention. The providing can include providing code to a user in any manner. For example, the providing can include transmitting digital signals containing the code to a user; providing the code on a physical media to a user; or any other method of making the code available.

Embodiments of the present invention can include a computer-implemented method for transmitting the code which can be executed at a computer to perform any of the processes of embodiments of the present invention. The transmitting can include transfer through any portion of a network such as the Internet; through wires, the atmosphere or space; or through any other type of transmission. The transmitting can include initiating a transmission of code; or causing the code to pass into any region or country from another region or country. A transmission to a user can include any transmission received by the user in any region or country, regardless of the location from which the transmission is sent.

A device for administering a medicament to a target tissue in a patient while simultaneously applying a vacuum to the target tissue comprising a vacuum cup 110, wherein the vacuum cup 110 includes one or more walls, an interior, and a vacuum connection, wherein the one or more walls form a lip which is applied to the target tissue. The device further comprising a membrane containing the medicament, wherein the membrane is located inside the vacuum cup 110 interior. The device also comprising a vacuum generator for applying a vacuum to the interior of the vacuum cup 110 and a vacuum connection, wherein the vacuum connection connects the vacuum to the vacuum cup 110 interior cavity. The device for administering a medicament to a target tissue in a patient while simultaneously applying a vacuum to the target tissue, wherein the membrane is selected from the group consisting of cross-linked gelatin, a gelatin sponge, oxidized regenerated cellulose, microfibrillar collagen, collagen sponges, hydrogels, polyethylene glycol gels and protein cross-linked gels. The device for administering a medicament to a target tissue in a patient while simultaneously applying a vacuum to the target tissue, wherein the medicament is selected from the group consisting of bovine thrombin, fibrin, cellulose, microfibrillar collagen and collagen sponges. The device for administering a medicament to a target tissue in a patient while simultaneously applying a vacuum to the target tissue, wherein the medicament is selected from the group of hemostatic agents consisting of thrombin, fibrin, platelets purified from serum and N-acetyl glucosamine. The device for administering a medicament to a target tissue in a patient while simultaneously applying a vacuum to the target tissue, further comprising a valve to one or both release and apply the vacuum to the vacuum cup 110. The device for administering a medicament to a target tissue in a patient while simultaneously applying a vacuum to the target tissue, further comprising a tensioning device to secure the vacuum cup 110 to the target tissue and a release mechanism for releasing one or both the tensioning device and the vacuum. The device for administering a medicament to a target tissue in a patient while simultaneously applying a vacuum to the target tissue, comprising a tensioning device to secure the vacuum cup 110 to the target tissue and a release mechanism for releasing one or both the tensioning device and the vacuum, wherein the tensioning device is selected from the group consisting of the vacuum connection, a control shaft, an elongated control shaft, a handle, one or more tensioning cords, one or more hooks coupled directly to the vacuum cup 110, one or more hooks coupled to the cup 110 via an elongated control shaft, and one or more hooks coupled to the cup 110 via a handle. The device for administering a medicament to a target tissue in a patient while simultaneously applying a vacuum to the target tissue, comprising a tensioning device to secure the vacuum cup 110 to the target tissue and a release mechanism for releasing one or both the tensioning device and the vacuum, wherein the tensioning device includes two or more features selected from the group consisting of the vacuum connection, a control shaft, an elongated control shaft, a handle, one or more tensioning cords, one or more hooks coupled directly to the vacuum cup 110, one or more hooks coupled to the cup 110 via an elongated control shaft, and one or more hooks coupled to the cup 110 via a handle. The device for administering a medicament to a target tissue in a patient while simultaneously applying a vacuum to the target tissue, comprising a tensioning device to secure the vacuum cup 110 to the target tissue and a release mechanism for releasing one or both the tensioning device and the vacuum, wherein the device is used to manipulate the target tissue while the medicament and vacuum are being administered.

A system for administering a therapeutic agent while applying a vacuum to a wound surface comprising a vacuum cup 110 including, an outer perimeter, a wall and a top, wherein the outer perimeter is positioned proximal to the wound surface, wherein when the vacuum cup 110 is applied to the wound surface the vacuum cup 110 and the wound surface enclose a cavity. The system further comprising a vacuum source, wherein the vacuum source applies a vacuum to the cavity, wherein applying the vacuum to the device collapses the walls of the vacuum cup 110 to one or both contract the wound surface and move the top closer to the wound surface and the therapeutic agent, wherein applying the vacuum to the device administers the therapeutic to the wound surface.

In an embodiment of the invention, a device for administering a therapeutic agent while applying a vacuum to a tissue surface comprises a vacuum cup including an outer perimeter, a wall and a top, where the outer perimeter is adapted to be positioned proximal to the tissue surface, a vacuum source adapted to apply a vacuum to the device and a temperature pump adapted to apply one or both heating and cooling to the tissue surface. The device further comprising one or both an inlet for introducing the therapeutic agent and the therapeutic agent.

In an embodiment of the invention, a device for administering a therapeutic agent while applying a vacuum to a tissue surface comprises a vacuum cup including an outer perimeter, a wall and a top, where the outer perimeter is adapted to be positioned proximal to the tissue surface, a vacuum source adapted to apply one or both a positive and negative pressure within the device and a temperature pump adapted to apply one or both heating and cooling to the tissue surface. The device further comprising one or both an inlet for introducing the therapeutic agent and the therapeutic agent.

In an embodiment of the invention, a device for administering a therapeutic agent while applying a vacuum to a tissue surface comprises a vacuum cup including an outer perimeter, a wall and a top, where the outer perimeter is adapted to be positioned proximal to the tissue surface and a vacuum source adapted to apply a vacuum to the device. The device further comprises a temperature pump adapted to apply one or both heating and cooling to the tissue surface and one or both an inlet for introducing the therapeutic agent and the therapeutic agent.

In an embodiment of the invention, a device for administering a therapeutic agent and a vacuum to a tissue surface comprises a vacuum cup including an outer perimeter, a wall and a top, where the outer perimeter is adapted to be positioned proximal to the tissue surface and a vacuum source adapted to apply both positive and negative pressure to the tissue surface. The device further comprises a temperature pump adapted to one or both heat and cool the temperature of the tissue surface and an inlet adapted for administering the therapeutic agent.

In an embodiment of the invention, a device for administering a therapeutic agent and a vacuum to a tissue surface comprises a vacuum cup including an outer perimeter, a wall and a top, where the outer perimeter is adapted to be positioned proximal to the tissue surface and a vacuum source adapted to apply one or both positive and negative pressure to the tissue surface. The device further comprises a temperature pump adapted to both heat and cool the temperature of the tissue surface and an inlet adapted for administering the therapeutic agent.

In an embodiment of the invention, a device for administering a therapeutic agent and a vacuum to a tissue surface comprises a vacuum cup including an outer perimeter, a wall and a top, where the outer perimeter is adapted to be positioned proximal to the tissue surface and a vacuum source adapted to apply both positive and negative pressure to the tissue surface. The device further comprises a temperature pump adapted both heat and cool the temperature of the tissue surface and an inlet adapted for administering the therapeutic agent.

In an embodiment of the invention, the therapeutic agent is one or more of impregnated, coated and dispersed in one or more materials selected from the group consisting of a biofilm, a cloth, an absorbent and a cotton-like substance, where the material is associated with one or both the top and the wall, where application of the vacuum brings the materials into contact with the tissue surface and dispenses the therapeutic agent.

In an embodiment of the invention, the therapeutic agent is located in a chamber within the device, where the chamber is adapted to dispense the therapeutic agent to the tissue surface. The device further comprising a relief valve adapted to apply the vacuum to the chamber.

The device further comprising a peel and shrink bandage. The device where the peel and shrink bandage is first applied to the tissue surface and the device is one or both attached or adhered to the peel and shrink bandage.

The device where the temperature pump is adapted to one or both increase and decrease the temperature of the tissue surface over time. The device where the temperature pump is adapted to one or both vasoconstrict and vasodilate the tissue surface. The device where the temperature pump includes a heat sink. The device where the heat sink includes a material that absorbs or releases energy to the heat sink.

In an embodiment of the invention, a method of delivering a medicament to a target tissue while a vacuum is applied to the target tissue comprises the steps of applying the medicament to a chamber within a vacuum cup and positioning the opening of the vacuum cup over target tissue, where the vacuum cup includes an interior cavity. The method further comprises applying one or both positive and negative pressure to one or more interior cavities of the vacuum cup through one or more connections, where that the vacuum cup becomes attached to the target tissue and delivering the medicament from the chamber to the target tissue. This method further comprises selecting the medicament from the group consisting of bovine thrombin plus cross-linked gelatin, fibrin sealants, gelatin sponge, oxidized regenerated cellulose, microfibrillar collagen and collagen sponges. This method alternatively comprises selecting the medicament from the group of hemostatic agents consisting of completely autologous fibrin sealants, platelets purified from serum combined with thrombin, completely synthetic hydrogels made from polyethylene glycol, bovine serum plus albumin plus glutaraldehyde and N-acetyl glucosamine.

The foregoing description of embodiments of the methods, systems, and components of the present invention has been provided for the purposes of illustration and description. It is not intended to be exhaustive or to limit the invention to the precise forms disclosed. Many modifications and variations will be apparent to one of ordinary skill in the relevant arts. For example, steps performed in the embodiments of the invention disclosed can be performed in alternate orders, certain steps can be omitted, and additional steps can be added. The embodiments were chosen and described in order to best explain the principles of the invention and its practical application, thereby enabling others skilled in the art to understand the invention for various embodiments and with various modifications that are suited to the particular used contemplated. Other embodiments are possible and are covered by the invention. Such embodiments will be apparent to persons skilled in the relevant art(s) based on the teachings contained herein. The breadth and scope of the present invention should not be limited by any of the above-described exemplary embodiments, but should be defined only in accordance with the following claims and their equivalents.

What is claimed is:

1. A device for compressing a tissue surface comprising:
a vacuum cup including an outer perimeter adapted to attach to the tissue surface when a negative pressure is applied in the vacuum cup, a top and a wall including a plurality of parallel ridges extending lengthwise from the top of the cup toward the outer perimeter aligned perpendicular to the tissue surface, where the outer perimeter, the wall and the top define two or more cavities, where the plurality of ridges assist one or both deformation and collapse of the wall when the negative pressure is applied in the vacuum cup, where the outer perimeter is adapted to be positioned proximal to the tissue surface; and
a vacuum source adapted to apply the negative pressure in the vacuum cup, where activation of the vacuum source evacuates air out of the vacuum cup such that when the outer perimeter is brought into contact with the tissue surface a negative pressure is generated in the vacuum cup which results in one or both the deformation and collapse of the wall and results in compression of the tissue surface.

2. The device of claim 1, where the tissue surface is a site of trauma.

3. The device of claim 2, where the compression of the tissue surface assists healing.

4. The device of claim 1, where the vacuum cup wall is adapted to controllably collapse on application of the negative pressure.

5. The device of claim 4, where collapse of the vacuum cup wall applies inward radial pull on the tissue surface.

6. The device of claim 4, where collapse of the vacuum cup wall creates one or both an axial compression and a radial constriction to the tissue surface.

7. The device of claim 4, where rate of the collapse of the vacuum cup wall is controlled by the negative pressure applied.

8. The device of claim 1, where the vacuum cup wall is constructed with a plurality of thicknesses corresponding to the plurality of ridges.

9. The device of claim 8, where the plurality of thicknesses of the vacuum cup wall assists in controlling one or both deformation and collapse of the vacuum cup wall under the negative pressure.

10. The device of claim 1, further comprising one or more of a membrane, a bead, a platform, a base and a cavity adapted for administering a therapeutic agent to the tissue surface.

11. The device of claim 10, further comprising a flexible bellows integral with the vacuum cup.

12. The device of claim 10, further comprising a relief valve to assist in controlling the negative pressure in the vacuum cup.

13. A device for administering a therapeutic to a tissue surface comprising:
a vacuum cup including an outer perimeter, a wall and a top, where the outer perimeter includes an inset positioned near the edge of the outer perimeter, where the outer perimeter is adapted to be positioned proximal to the tissue surface;
a bead adapted to be inserted in the inset, where the inset and the bead administer a therapeutic agent to the tissue surface via the exterior surface of the bead; and
a vacuum source adapted to apply negative pressure inside the vacuum cup, where the negative pressure deforms the wall in a controlled manner to administer the therapeutic agent to the tissue surface.

14. The device of claim 13, where an adhesion agent is associated with the outer perimeter to assist the bead to attach to the tissue surface.

15. The device of claim 13, further comprising a relief valve and a pump to generate a positive pressure, where the pump can supply the positive pressure to the relief valve.

16. The device of claim 13, where the therapeutic agent is one or more of impregnated, coated, sprayed and dispersed on the bead.

17. The device of claim 2, where the application of the negative pressure seals the site of trauma.

18. A device for administering a therapeutic to a tissue surface comprising:
a vacuum cup including a wall with a plurality of ridges forming an annular pattern with respect to the cup wall, where the plurality of ridges are perpendicular to the tissue surface and a top;
one or more of a membrane, a bead, a platform, a base and a cavity; and
a vacuum source adapted to apply negative pressure inside the vacuum cup, where the plurality of ridges assist one or both deformation and collapse of the wall when a negative pressure is applied in the vacuum cup, where the bead administers the therapeutic along the length of the bead.

19. The device of claim 18, where the therapeutic agent is located outside of the device and the wall deforms to bring the top into contact with the tissue surface for administering the therapeutic agent to the tissue surface.

20. The device of claim 18, where the compression of the tissue surface arrests the flow of blood.

* * * * *